United States Patent
Greene et al.

(10) Patent No.: US 10,499,832 B2
(45) Date of Patent: Dec. 10, 2019

(54) REFLECTOR MARKERS AND SYSTEMS AND METHODS FOR IDENTIFYING AND LOCATING THEM

(71) Applicant: CIANNA MEDICAL, INC., Aliso Viejo, CA (US)

(72) Inventors: John E. Greene, Valley Center, CA (US); Nikolai Rulkov, San Diego, CA (US); Jonathan White, Aliso Viejo, CA (US)

(73) Assignee: CIANNA MEDICAL, INC., Aliso Viejo, CA (US)

( * ) Notice: Subject to any disclaimer, the term of this patent is extended or adjusted under 35 U.S.C. 154(b) by 91 days.

(21) Appl. No.: 15/481,431

(22) Filed: Apr. 6, 2017

(65) Prior Publication Data

US 2017/0319102 A1 Nov. 9, 2017

Related U.S. Application Data

(63) Continuation-in-part of application No. 14/934,019, filed on Nov. 5, 2015.

(Continued)

(51) Int. Cl.
*A61B 5/06* (2006.01)
*A61B 34/20* (2016.01)
(Continued)

(52) U.S. Cl.
CPC .............. *A61B 5/064* (2013.01); *A61B 34/20* (2016.02); *A61B 90/04* (2016.02); *A61B 90/39* (2016.02); *A61B 90/98* (2016.02); *H01L 23/60* (2013.01); *H01L 25/167* (2013.01); *A61B 5/062* (2013.01); *A61B 2017/008* (2013.01); *A61B 2017/0088* (2013.01); *A61B 2017/00212* (2013.01);
(Continued)

(58) Field of Classification Search
CPC .................... A61B 5/064; A61B 90/39; A61B 2090/3904–3995; A61B 2017/00796–008
See application file for complete search history.

(56) References Cited

U.S. PATENT DOCUMENTS

| | | | | |
|---|---|---|---|---|
| 5,320,098 A | * | 6/1994 | Davidson | ............ A61N 5/0601 128/908 |
| 5,387,259 A | * | 2/1995 | Davidson | ............ A61N 5/0601 128/908 |

(Continued)

*Primary Examiner* — Eric D. Bertram
(74) *Attorney, Agent, or Firm* — William A. English; Vista IP Law Group LLP

(57) ABSTRACT

Markers and related systems and methods are provided for localizing lesions within a patient's body, e.g., within a breast. The marker includes one or more photosensitive diodes for transforming light pulses striking the marker into electrical energy, one or more antennas, and a switch coupled to the photodiodes and antennas such that the light pulses cause the switch to open and close and modulate radar signals reflected by the marker back to a source of the signals. The antenna(s) may include one or more wire elements extending from a housing, one or more antenna elements printed on a substrate, or one or more chip antennas. Optionally, the marker may include a processor coupled to the photodiodes for identifying signals in the light pulses or one or more coatings or filters to allow selective activation of the marker.

21 Claims, 18 Drawing Sheets

Related U.S. Application Data

(60) Provisional application No. 62/474,085, filed on Mar. 21, 2017, provisional application No. 62/319,225, filed on Apr. 6, 2016, provisional application No. 62/171,804, filed on Jun. 5, 2015.

(51) Int. Cl.

| | | |
|---|---|---|
| *A61B 90/00* | (2016.01) | |
| *A61B 90/98* | (2016.01) | |
| *H01L 23/60* | (2006.01) | |
| *H01L 25/16* | (2006.01) | |
| *A61B 17/00* | (2006.01) | |
| *A61B 90/30* | (2016.01) | |
| *A61B 34/30* | (2016.01) | |
| *H01L 23/00* | (2006.01) | |

(52) U.S. Cl.
CPC ........... *A61B 2017/00411* (2013.01); *A61B 2017/00867* (2013.01); *A61B 2034/2051* (2016.02); *A61B 2034/306* (2016.02); *A61B 2090/306* (2016.02); *A61B 2090/397* (2016.02); *A61B 2090/3908* (2016.02); *A61B 2090/3975* (2016.02); *A61B 2090/3979* (2016.02); *A61B 2090/3987* (2016.02); *H01L 24/48* (2013.01); *H01L 2224/48091* (2013.01); *H01L 2224/48227* (2013.01); *H01L 2224/48465* (2013.01); *H01L 2924/00014* (2013.01)

(56) References Cited

U.S. PATENT DOCUMENTS

| | | | |
|---|---|---|---|
| 6,492,933 B1* | 12/2002 | McEwan | G01S 13/582 342/118 |
| 6,725,083 B1* | 4/2004 | Burbank | A61K 49/006 600/414 |
| 6,898,464 B2* | 5/2005 | Edell | A61B 5/0017 128/903 |
| 9,987,097 B2* | 6/2018 | van der Weide | A61B 90/39 |
| 2003/0018246 A1* | 1/2003 | Govari | A61B 5/06 600/407 |
| 2007/0027505 A1* | 2/2007 | Ginggen | A61B 5/0031 607/60 |
| 2007/0038014 A1* | 2/2007 | Cox | A61N 5/1027 600/8 |
| 2011/0166442 A1* | 7/2011 | Sarvazyan | A61B 5/06 600/424 |
| 2011/0313288 A1* | 12/2011 | Chi Sing | A61B 5/0507 600/437 |
| 2017/0042622 A1* | 2/2017 | Yang | A61B 5/055 |

* cited by examiner

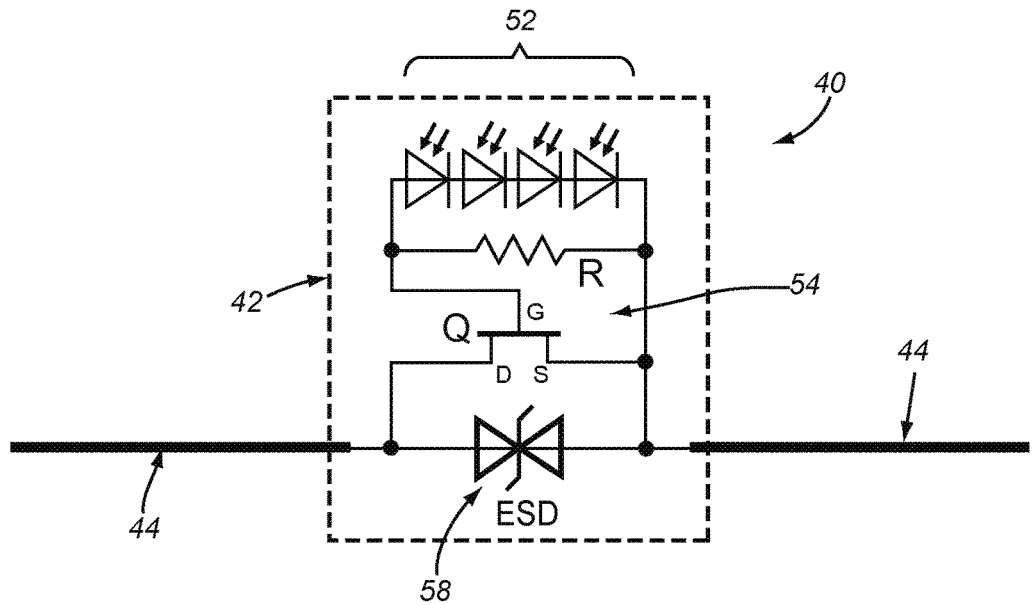
FIG. 2
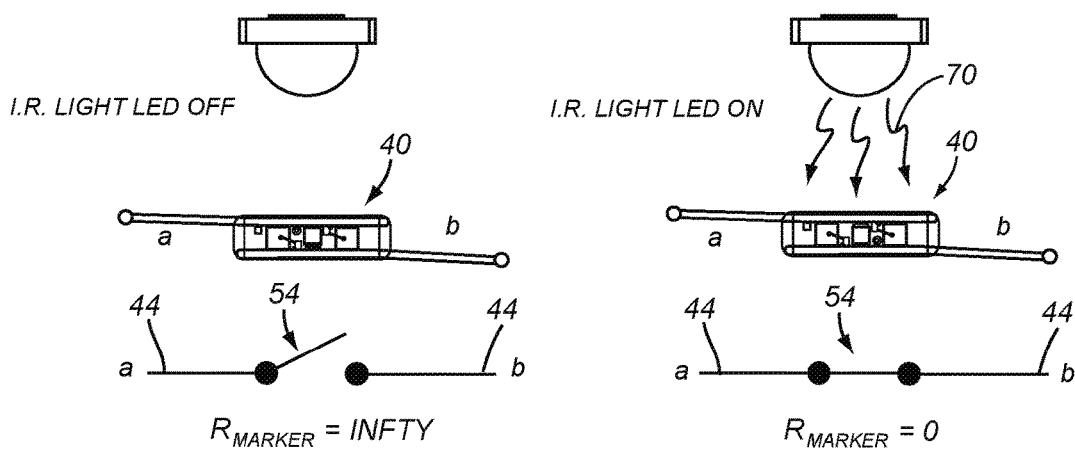
FIG. 3A
FIG. 3B

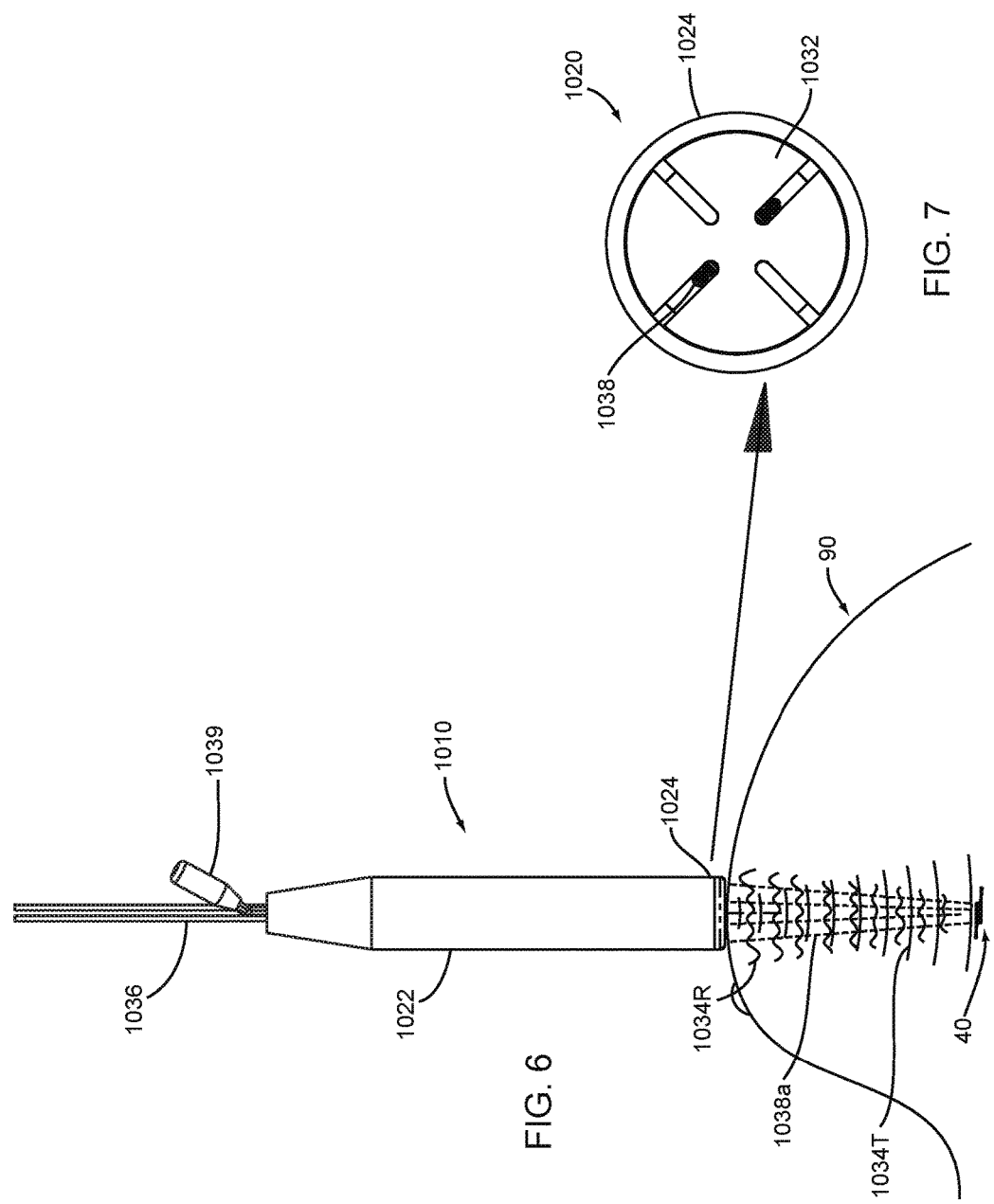

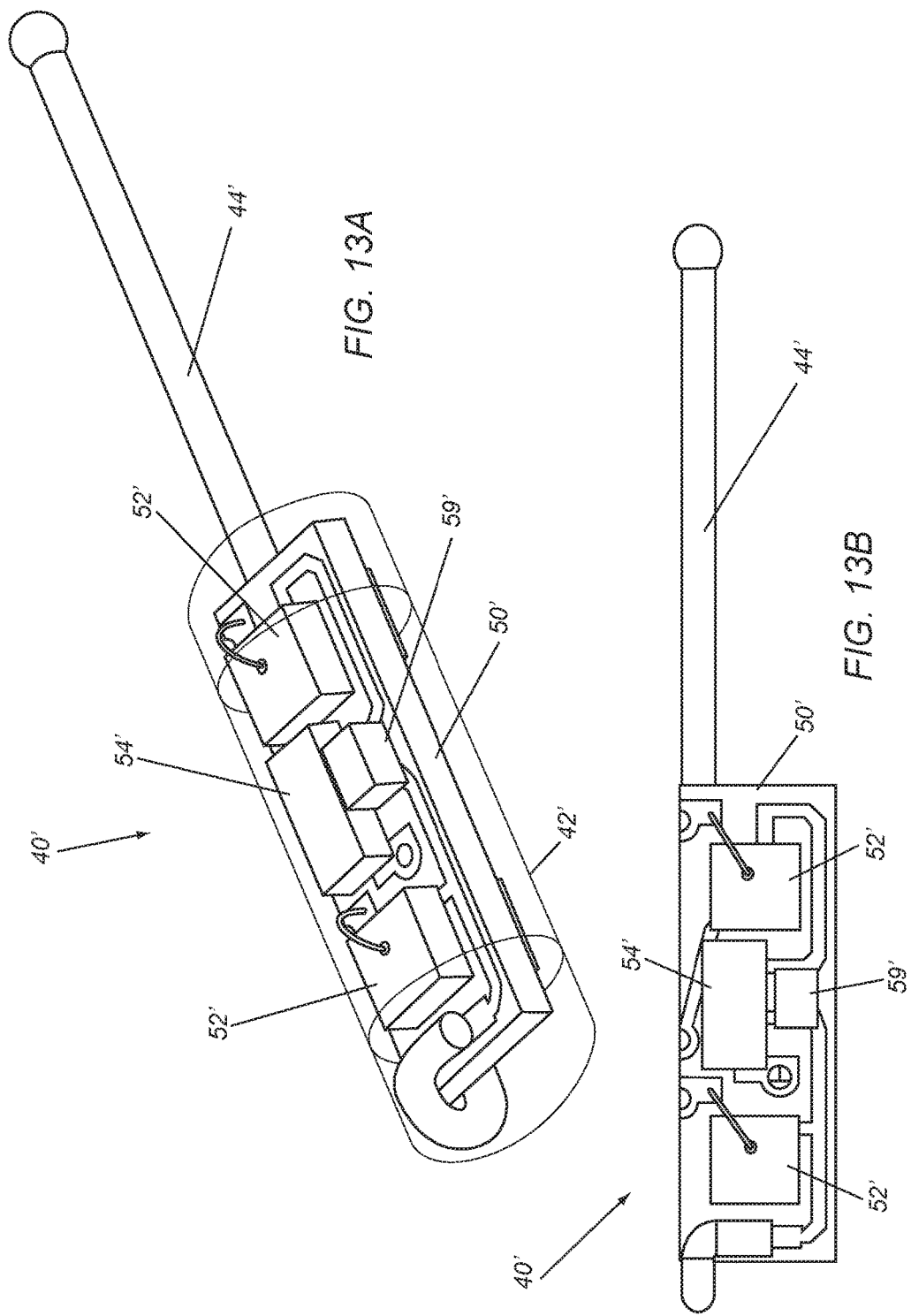

I-Q output vector

//  REFLECTOR MARKERS AND SYSTEMS AND METHODS FOR IDENTIFYING AND LOCATING THEM

RELATED APPLICATION DATA

The present application claims benefit of co-pending provisional applications Ser. Nos. 62/319,225, filed Apr. 6, 2016, and 62/474,085, filed Mar. 21, 2017, and is a continuation-in-part of co-pending application Ser. No. 14/934,019, filed Nov. 5, 2015, which claims benefit of provisional application Ser. No. 62/171,804, filed Jun. 4, 2015, the entire disclosures of which are expressly incorporated by reference herein.

FIELD OF THE INVENTION

The present invention relates to implantable markers or tags, and to systems and methods for localizing such markers within a patient's body, e.g., during surgical procedures or other procedures, such as during lumpectomy procedures.

BACKGROUND

Before a biopsy or surgical procedure to remove a lesion within a breast, e.g., during a lumpectomy procedure, the location of the lesion must be identified. For example, mammography or ultrasound imaging may be used to identify and/or confirm the location of the lesion before the procedure. The resulting images may be used by a surgeon during the procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization, immediately before a procedure, a wire may be inserted into the breast, e.g., via a needle, such that a tip of the wire is positioned at the location of the lesion. Once the wire is positioned, it may be secured in place, e.g., using a bandage or tape applied to the patient's skin where the wire emerges from the breast. With the wire placed and secured in position, the patient may proceed to surgery, e.g., to have a biopsy or lumpectomy performed.

One problem with using a wire for localization is that the wire may move between the time of placement and the surgical procedure. For example, if the wire is not secured sufficiently, the wire may move relative to the tract used to access the lesion and consequently the tip may misrepresent the location of the lesion. If this occurs, when the location is accessed and tissue removed, the lesion may not be fully removed and/or healthy tissue may be unnecessarily removed. In addition, during the procedure, the surgeon may merely estimate the location of the wire tip and lesion, e.g., based on mammograms or other images obtained during wire placement, and may proceed with dissection without any further guidance. Again, since such images are two dimensional, they may provide limited guidance to localize the lesion being treated or removed.

Alternatively, it has been suggested to place a radioactive seed to provide localization during a procedure. For example, a needle may be introduced through a breast into a lesion, and then a seed may be deployed from the needle. The needle may be withdrawn, and the position of the seed may be confirmed using mammography. During a subsequent surgical procedure, a hand-held gamma probe may be placed over the breast to identify a location overlying the seed. An incision may be made and the probe may be used to guide excision of the seed and lesion.

Because the seed is delivered through a needle that is immediately removed, there is risk that the seed may migrate within the patient's body between the time of placement and the surgical procedure. Thus, similar to using a localization wire, the seed may not accurately identify the location of the lesion, particularly, since there is no external way to stabilize the seed once placed. Further, such gamma probes may not provide desired precision in identifying the location of the seed, e.g., in three dimensions, and therefore may only provide limited guidance in localizing a lesion.

Accordingly, apparatus and methods for localization of lesions or other tissue structures in advance of and/or during surgical, diagnostic, or other medical procedures would be useful.

SUMMARY

The present invention is directed to implantable markers and tags, and to systems and methods for localizing such markers within a patient's body, e.g., during surgical procedures or other procedures, such as during lumpectomy procedures.

In accordance with one embodiment, a marker is provided sized for introduction into a target tissue region within a patient's body that includes an energy converter for transforming energy pulses striking the marker into electrical energy; a switch coupled to the energy converter such that the energy pulses cause the switch to open and close; and one or more antennas coupled to the switch, the switch configured to open and close to modulate radar signals reflected by the marker back to a source of the signals. The antenna(s) may include one or more wire elements extending from a housing of the marker, one or more antenna elements printed on a substrate, or one or more chip antennas. Optionally, the marker may include one or more additional components, such as an electro static discharge (ESD) protection device coupled to the switch to provide protection against an electrostatic discharge event, a processor coupled to the energy converter for identifying signals in the energy pulses, one or more coatings or filters, and the like.

In accordance with another embodiment, a marker is provided for introduction into a target tissue region within a patient's body that includes one or more photosensitive diodes configured to convert light pulses received from a light source to generate a voltage; a switch; one or more antennas coupled to the switch; and a processor coupled to the one or more photosensitive diodes and the switch, the processor configured to analysis light pulses received by the one or more photosensitive diodes to identify a first predetermined bit code in the light pulses, the processor delivering the voltage from the one or more photosensitive diodes to the switch to cause the switch to open and close only after the light pulses include the first predetermined bit code, the switch configured to open and close to modulate signals reflected by the one or more antennas back to a source of the signals.

In accordance with still another embodiment, a marker is provided for introduction into a target tissue region within a patient's body that includes one or more photosensitive diodes configured to convert light pulses received from a light source to generate a voltage; a switch; one or more antennas coupled to the switch; and a housing containing the one or more photosensitive diodes and the switch, the housing comprising a filter or coating overlying the one or more photosensitive diodes, the filter or coating only permitting a predetermined segment of infrared light to strike the one or more photosensitive diodes.

In accordance with another embodiment, a plurality of markers are provided for introduction into a target tissue region within a patient's body, each marker including one or more photosensitive diodes configured to convert light pulses received from a light source to generate a voltage; a switch; one or more antennas coupled to the switch; and a processor coupled to the one or more photosensitive diodes and the switch. The processor of each marker is configured to analysis light pulses received by the one or more photosensitive diodes to identify a predetermined bit code in the light pulses, the processor delivering the voltage from the one or more photosensitive diodes to the switch to cause the switch to open and close only after the light pulses include the predetermined bit code, the switch configured to open and close to modulate signals reflected by the one or more antennas back to a source of the signals, and wherein the predetermined bit code is different for each marker.

In accordance with still another embodiment, a plurality of markers is provided for introduction into a target tissue region within a patient's body, each marker including one or more photosensitive diodes configured to convert light pulses received from a light source to generate a voltage; a switch; one or more antennas coupled to the switch; and a housing containing the one or more photosensitive diodes and the switch, the housing comprising a filter or coating overlying the one or more photosensitive diodes, the filter or coating only permitting a predetermined segment of infrared light to strike the one or more photosensitive diodes, wherein the predetermined segment of infrared light is different for each marker.

In accordance with yet another embodiment, a system is provided for localization of a target tissue region within a patient's body that includes a probe including one or more antennas for transmitting electromagnetic signals into a patient's body and receiving reflected signals from the patient's body, and an energy source for delivering energy pulses into a patient's body. The system also includes a marker sized for implantation within a patient's body, the marker including an energy converter configured to transform the energy pulses from the energy source into electrical energy, a switch coupled to the energy converter such that the energy pulses cause the switch to open and close to modulate the electromagnetic signals from the probe reflected by the marker, and one or more antennas coupled to the switch, the switch configured to open and close to modulate radar signals reflected by the marker back to a source of the signals.

In accordance with another embodiment, a method is provided for localization of a target tissue region within a patient's body that includes implanting a marker within a patient's body, the marker including a switch, an energy converter, and one or more antennas; placing a probe adjacent the patient's body oriented towards the marker; and activating the probe to a) transmit electromagnetic signals into the patient's body, b) receive reflected signals from the patient's body, and c) deliver energy pulses into the patient's body such that the energy converter transforms the energy pulses into electrical energy to open and close the switch to modulate the electromagnetic signals from the probe reflected by the marker. The switch and antennas may modify an impedance of the marker and/or tissue within which the marker is implanted, e.g., in response to the electromagnetic signals that strike the marker. In an exemplary embodiment, delivering energy pulses into the patient's body may include delivering infrared light into the patient's body, and the energy converter may include one or more photosensitive diodes that transform the infrared light into electrical energy to open and close the switch to modulate the electromagnetic signals from the probe reflected by the marker. In addition, the probe may provide information related to the location of the marker within the patient's body and/or relative to the probe.

In accordance with still another embodiment, a system is provided for identifying a marker implanted within a target tissue region, that includes a probe comprising one or more antennas for transmitting a radar signal into a patient's body towards a marker and receiving a reflected signal from the marker, and a light source for delivering infrared light pulses into the patient's body to cause the marker to change its reflective properties; a wave generator for generating a substantially continuous wave; a divider coupled to the wave generator for dividing the wave into first and second signals, the first signal delivered to the one or more antennas to transmit a substantially continuous transmit signal; a mixer coupled to the power divider for receiving the second signal and coupled to the one or more antennas for receiving the reflected signal, the mixer mixing the second signal and the reflected signal to produce an IF signal comprising components associated with modulation of amplitude and phase of the reflected signal caused by the light pulses changing the reflective properties of the marker; and a processor coupled to the mixer comprising a synchronous modulation detector that processes the IF signal to provide an output identifying and/or indicative of range from the one or more antennas to the marker based at least in part on the modulation of amplitude and phase synchronous with the light pulses delivered by the light source.

In accordance with yet another embodiment, a method is provided for localization of a marker within a target tissue region within a patient's body that includes implanting a marker within a patient's body; placing a tip of a probe adjacent the patient's body oriented towards the marker; and activating the probe to a) transmit a substantially continuous radar signal into the patient's body, b) receive a reflected signal from the patient's body, c) in synchronization with transmitting the radar signal, deliver light pulses into the patient's body such that the marker transforms the light pulses into electrical energy to open and close a switch in the marker to modulate the reflected signal reflected by the marker, and d) process the reflected signal using a synchronous detector to measure amplitude of modulation caused by the light pulses and provide an output identifying and/or indicative of range from the tip of the probe to the marker.

In accordance with another embodiment, a system is provided for localization of a marker within a target tissue region within a patient's body that includes a probe comprising one or more antennas for transmitting a radar signal into a patient's body towards a marker and receiving a reflected signal from the marker, and a light source for delivering infrared light pulses into the patient's body to cause the marker to change its reflective properties; a signal generator for generating a substantially continuous wave; a divider coupled to the signal generator for dividing the wave into first and second signals, the first signal delivered to the one or more antennas to transmit a substantially continuous transmit signal; a phase splitter coupled to the divider for receiving the second signal creating a replica signal out of phase with the second signal; first and second mixers coupled to the phase splitter for receiving the second signal and the replica signal, respectively, and coupled to the one or more antennas for receiving the reflected signal such that the first mixer mixes the second signal and the reflected signal and the second mixer mixes the replica signal and reflected signal to produce IF signals comprising components associated with modulation of amplitude and phase of the reflected signal caused by the light pulses changing the reflective properties of the marker; and a processor coupled to the mixers comprising a synchronous modulation detector that processes the IF signals to provide an output indicative of range from the one or more antennas to the marker based at least in part on the modulation of amplitude and phase synchronous with the light pulses delivered by the light source.

In accordance with still another embodiment, a method is provided for localization of a marker implanted within a target tissue region within a patient's body that includes placing a tip of a probe adjacent the patient's body oriented towards the marker; activating the probe to transmit a substantially continuous radar signal into the patient's body, receive a reflected signal from the patient's body, and in synchronization with transmitting the radar signal, deliver light pulses into the patient's body such that the marker transforms the light pulses into electrical energy to open and close a switch in the marker to modulate the reflected signal reflected by the marker; mixing the return signal with a source signal used to generate the substantially continuous radar signal and a phase-shifted replica of the source signal to produce IF signals comprising components associated with modulation of amplitude and phase of the reflected signal caused by the light pulses changing the reflective properties of the marker; and processing the IF signals to provide an output indicative of range from the one or more antennas to the marker based at least in part on the modulation of amplitude and phase synchronous with the light pulses delivered by the light source.

Other aspects and features of the present invention will become apparent from consideration of the following description taken in conjunction with the accompanying drawings.

BRIEF DESCRIPTION OF THE DRAWINGS

These and other features, aspects, and advantages of the present disclosure will become better understood with regard to the following description, appended claims, and accompanying drawings where:

FIG. 2 is an exemplary embodiment of a schematic of a circuit that may be included in the marker of FIG. 1.

FIGS. 3A and 3B are schematics demonstrating operation of a switch of the circuit of FIG. 2.

FIG. 6 is a side view of an exemplary embodiment of a probe and a marker implanted within a breast.

FIG. 7 is an end view of a distal end of the probe of FIG. 6.

FIGS. 13A and 13B are perspective and top views, respectively, of still another exemplary embodiment of a marker for implantation within a patient's body.

DETAILED DESCRIPTION OF THE EXEMPLARY EMBODIMENTS

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 1:
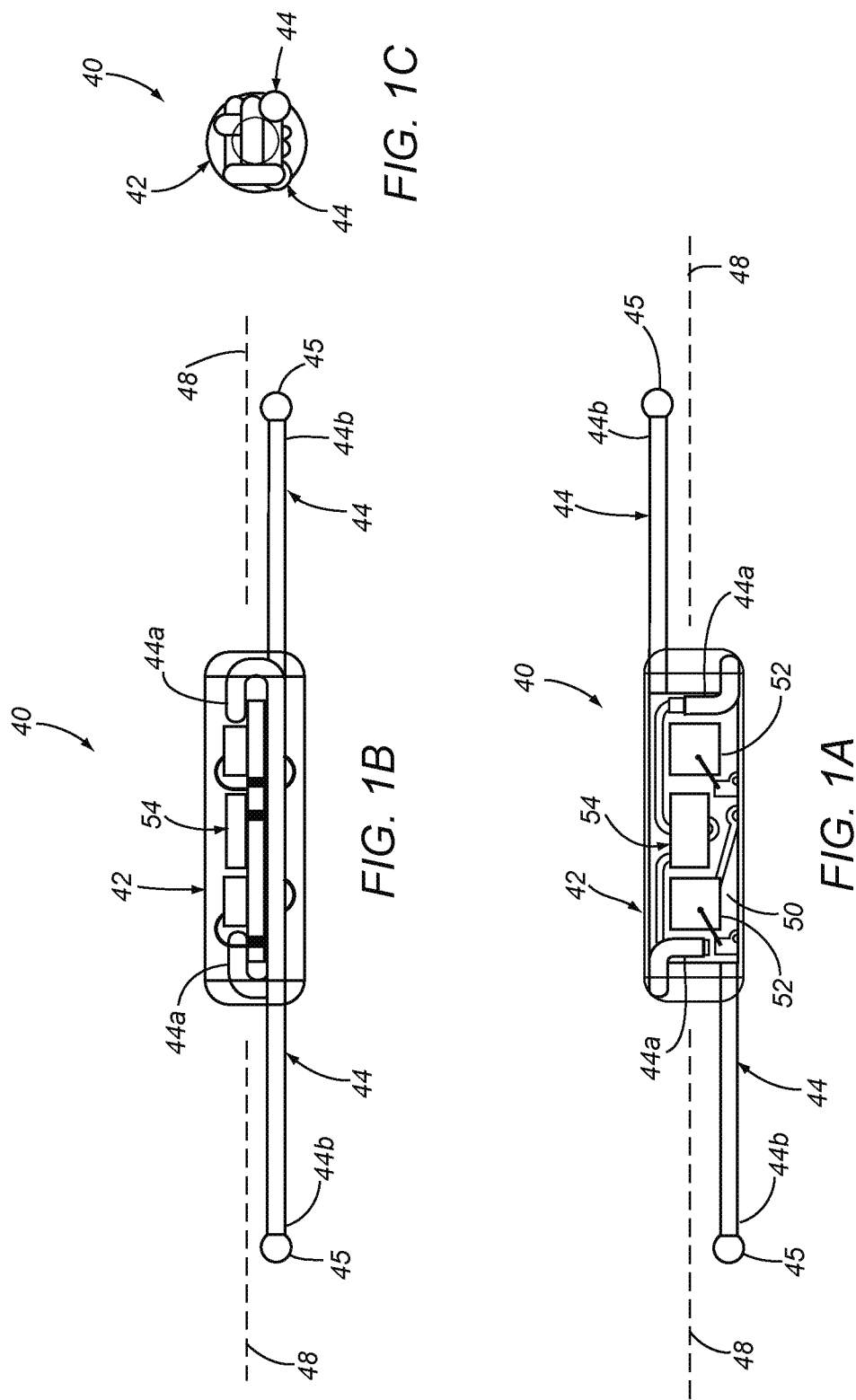
FIGS. 1A-1C are top, side, and end views, respectively, of an exemplary embodiment of a marker for implantation within a patient's body.
Figure 8:
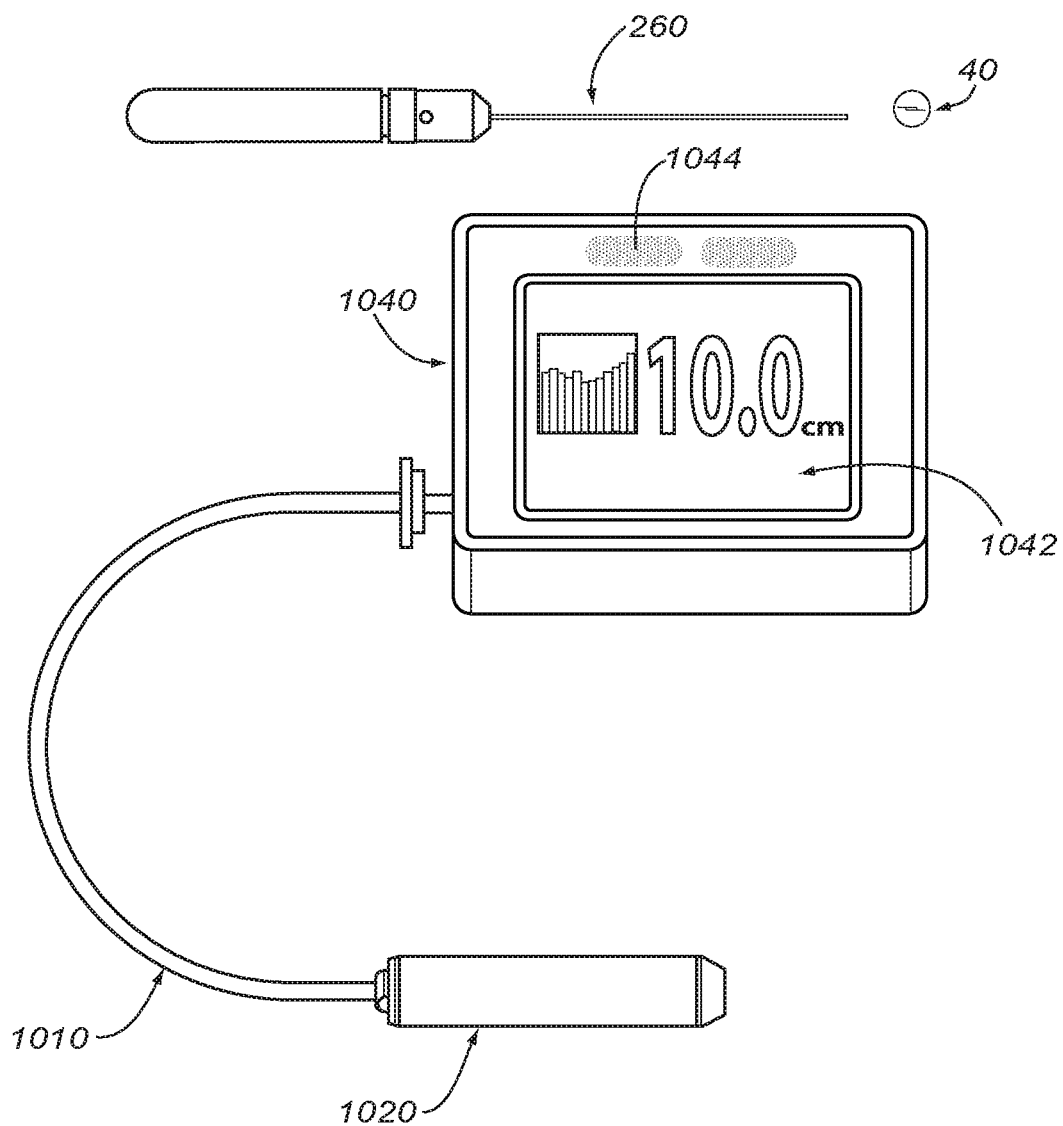
FIG. 8 is a schematic representation of exemplary components of a system for localizing a marker.

Turning to the drawings, FIGS. 1A-1C show an exemplary embodiment of a reflector marker or tag 40 that may be implanted within a patient's body, such as within a breast 90, e.g., as shown in FIG. 6. Generally, the marker 40 includes an electronics package 42 coupled to one or more wires or other antennas 44. The marker 40 may be included in a system 1010 for performing a procedure, such as a lumpectomy procedure, e.g., including a delivery device (not shown, see, e.g., FIG. 8) for delivering one or more of the markers into tissue, a probe 1020 for locating marker(s) implanted within tissue, and/or other components, e.g., as shown in FIGS. 6-8 and described further below.

In an exemplary embodiment, each antenna 44 may be an elongate member, e.g., a solid or hollow structure having a diameter or other maximum cross-section between about half and two millimeters (0.5-2 mm) and a length between about one and ten millimeters (1.0-10 mm). The antennas 44 may be formed from elastic or superelastic material and/or from shape memory material, e.g., stainless steel, Nitinol, and the like, such that the antennas 44 are biased to a predetermined shape when deployed within tissue, but may be elastically deformed, e.g., to facilitate delivery, as explained elsewhere herein. As described elsewhere herein, the antennas 44 may act to modify a resonance impedance of the marker and/or tissue within which the marker 40 is implanted, e.g., in response to radar or other electromagnetic signals that strike the marker 40, to enhance detecting and/or locating the marker 40 within a patient's body.

Optionally, the antennas 44 may carry one or more beads or other elements (not shown), e.g., similar to embodiments described in the applications incorporated by reference herein. For example, the antennas 44 may include core wires that carry a plurality of beads or segments (not shown) including multiple surfaces, angles, and/or edges to enhance detection of the marker 40. In an exemplary embodiment, the beads may include a plurality of individual annular bodies, e.g., each defining a portion of a generally cylindrical or spherical shape.

As shown in FIGS. 1A-1C, the antennas 44 may be biased to assume a substantially linear configuration, e.g., such that the antennas 44 extend substantially parallel to a longitudinal axis 48 of the marker 40. Alternatively, the antennas 44 may be substantially rigid such that the marker 40 remains in a substantially fixed, e.g., linear or curved, shape. Optionally, one or both antennas 44 may be offset from the longitudinal axis 48, which may enhance loading the marker 40 within a delivery device (not shown), as described elsewhere herein or in the applications incorporated by reference herein.

As best seen in FIG. 1A, each antenna 44 may include a first end 44a coupled to a printed circuit board (PCB) or other substrate 50 within the package 42 and a second free end 44b terminating in an enlarged and/or rounded tip 45. Optionally, the first ends 44a may include one or more bends, e.g., to facilitate coupling the first ends 44a to the substrate 50 and/or such that the antennas 44 extend tangentially from opposite sides of the package 42, as best seen in FIG. 1A.

Alternatively, the antennas 44 may be biased to assume a curvilinear or other configuration, e.g., a helical, serpentine or other curved shape, around the longitudinal axis 48. For example, the antennas 44 may be formed from elastic or superelastic material that is shape set such that the antennas 44 are biased to a helical configuration (not shown), yet may be resiliently straightened to a substantially linear configuration, e.g., to facilitate loading the marker 40 into a delivery device and/or otherwise introducing the marker 40 into a patient's body, e.g., as described in U.S. applications Ser. No. 14/165,253, filed Jan. 27, 2014, U.S. Ser. No. 13/053,197, filed Mar. 21, 2011, and U.S. Ser. No. 12/824,139, filed Jun. 25, 2010, the entire disclosures of which are expressly incorporated by reference herein.

With additional reference to FIG. 2, the marker 40 may include one or more circuits or other electrical components encased or embedded in the electronics package 42 and configured to modulate incident signals from a probe (not shown, such as the probe 1020 shown in FIG. 6 and described elsewhere herein) used to locate the marker 40, also as described elsewhere herein. For example, the components may be provided on a semiconductor chip, print circuit board (PCB), and/or other substrate 50 carried in the package 42. In an exemplary embodiment, the components may include a voltage or power source or other power or energy converter 52, a switch 54 that may be opened and closed when the energy converter 52 generate electrical energy, and an Electro Static Discharge (ESD) protection device 58, e.g., mounted or otherwise provided on the substrate 51.

The components may be encased within one or more components defining the package 42. In an exemplary embodiment, the components may be soldered, glued, or otherwise mounted on a surface of the substrate 50 and encapsulated in epoxy or other insulating and/or protective material (not shown). For example, the components may be mounted within the package 42 such that the components are electrically isolated from one another other than as coupled in the schematic of FIG. 2. Optionally, shrink tubing or other outer body may be applied around the epoxy material, e.g., to provide a desired finish and/or outer surface for the marker 40.

In an exemplary embodiment, the energy converter 52 includes a plurality of photosensitive diodes capable of transforming incident light (e.g., infrared light) striking them into electrical energy (e.g., a predetermined minimum voltage). As shown, multiple pairs of diodes 52 may be connected in series, which may be arranged orthogonally to one another spatially within the package 42. For example, given that photosensitive diodes are directional, at least two pairs of diodes 52 may be mounted within the package 42 offset one hundred eighty degrees (180°) or otherwise relative to one another, e.g., as best seen in FIG. 1A, such that at least one pair of diodes 52 may receive light from a light transmitter of the probe 1020 regardless of the orientation of the marker 40 relative to the probe 1020 after implantation. The package 42 may be at least partially transparent or the diodes 52 may be exposed such that light directed towards the package 42 may be received by the diodes 52.

Optionally, the diodes 52 and/or any surfaces of the package 42 overlying the diodes 52 may include one or more coatings, filters, and the like (not shown), e.g., formed on the shrink tubing or other components of the package 42, to limit the light that strikes the diodes 52 in a desired manner. For example, one or more coatings may be provided that only permit a desired band width of infrared light to strike the diodes 52. In this manner, multiple markers may be provided that allow different band widths to activate the respective markers, e.g., such that a probe may activate a desired marker by transmitting infrared red limited to the particular band width of the desired marker.

In alternative embodiments, the energy converter 52 may include other components capable of transforming external energy into a desired voltage. For example, if the probe 1020 includes another power source, e.g., a source of EMF, RF, or vibrational energy, the energy converter 52 may include a pick-up coil, antenna, or other device capable of transforming the incident energy into the desired voltage, e.g., including a capacitor and/or other components arranged to deliver the desired voltage to the switch 54. One advantage of infrared energy is that it may pass sufficiently through tissue such that a probe 1020 placed against a patient's skin may deliver sufficient energy to activate a relatively small marker 40 implanted several inches away within the patient's body, e.g., within a breast 90, as shown in FIG. 6.

In the embodiment shown in FIG. 2, the switch 54 may be a field effect transistor (FET), e.g., a junction field effect transistor (JFET), with one end of the diodes 52 coupled to the gate (G) and the other coupled to the source (S), with a resistor 56 coupled between the gate (G) and the source (S), e.g., to discharge the diodes 52 when there is no IR light. In an exemplary embodiment, the switch 54 may include an enhancement mode pseudomorphic high electron mobility transistor (E-pHEMT), such as a VMMK-1225 manufactured by Avago Technologies US Inc., and the resistor 56 may be a three mega-Ohm (3MΩ) resistor. In an alternative embodiment, the switch 54 may be a Schottky diode coupled to the diodes 52 (or other voltage source), e.g., with opposite ends of the diode coupled to the antennas 44.

Also as shown, the source (S) of the switch 54 may be electrically coupled to one of the antennas 44 and the drain (D) may be coupled to the other antenna 44. The antennas 44 may be bonded or otherwise attached to the package 42 such that ends of the antennas 44 are electrically coupled to the switch 54 as shown.

Each diode 52 may be capable of generating sufficient voltage (e.g., about a half Volt (0.5 V)) when exposed to light to open and close the switch 54 when there is little or no load (i.e., current draw). Since the resulting circuit is intended to modulate signals from the probe 1020, little or no current is needed, and so the power required from the diodes 52 (and consequently from the probe 1020) may be minimal, thereby reducing power demands of the marker 40 and probe 1020.

With additional reference to FIGS. 3A and 3B, light intermittently striking the diodes 52 may generate a voltage across the gate (G) and source (S) to provide a control signal that may open and close the switch 54. For example, FIG. 3A shows the switch 54 in the open configuration when infrared light is absent, while FIG. 3B shows the switch 54 in the closed configuration when infrared light 70 strikes the diodes 52, thereby connecting both antennas 44 together. Thus, the result is that the marker 40 provides a passive reflector tag that includes what equates to a high-frequency switch in the middle of the marker 40. By being able to change the switch 54 from closed to open, the reflective properties of the effective antenna provided by the antennas 44 may be changed significantly. For example, the switch 54 may change the polarity or otherwise modulate signals reflected from the marker 40 as the switch 54 is opened and closed and/or may change a resonance impedance of the marker 40 and/or tissue within which the marker 40 is implanted.

Some of the challenges involved in detecting markers implanted within breast tissue (or elsewhere in a patient's body) include the relatively small radar cross-section (RCS) of such markers and contamination of the received reflected signal, e.g., due to (a) scattering caused by tissue inhomogeneity; (b) cross-talk between transmit and receive antennas of the probe; and (c) signal distortions due to near field effects and other factors. To deal with these complicating factors and distinguish the reflected marker signal from contaminating signals received by the probe, the switch 54 provides periodic modulation of reflective properties of the marker 40.

Specifically, the marker 40 is made to periodically change its structure between two form factors, e.g., the reflectors shown in FIGS. 3A and 3B. For example, as described further elsewhere herein, digital signal processing of the received signals using ultra-wideband (UWB) radar uses synchronous detection of the signal modulated with marker switching frequency. This significantly increases the signal-to-noise (SNR) on the marker signal because other contaminating signals remain unchanged within the modulation period. To provide a mechanism for a synchronous detector, the marker switching process is controlled in the probe 1020 by illuminating breast tissue with near infrared (IR) light pulses that are received by the marker 40.

Switching of the marker reflective form-factor is controlled with the set of diodes 52 operating in photovoltaic mode. When the diodes 52 receive light from the probe 102 (represented by arrows 70 in FIG. 3B), the diodes 52 generate voltage that is applied between the gate (G) and source (S) of the switch 54, which closes and connects together the drain (D) and source (S) making both antenna wires 44 connected together, as shown in FIG. 3B. When the light is off, the switch 54 is open and the drain (D) and source (S) are electrically disconnected, as shown in FIG. 3A.

In addition, the ESD device 58 may be coupled in parallel across the switch 54, e.g., between the drain (D) and source (S), to provide protection against an electrostatic discharge event. For example, use of an E-pHEMT device as switch 54 sets restrictions on the absolute maximal voltage between the drain (D) and source (S) and, therefore, across the marker's antennas. In the exemplary embodiment of a VMMK-1225 E-pHEMT, the maximal voltage across the switch 54 may be no more than about five Volts (5 V). Modern breast surgery often involves the use of electro-cutting tools, electocautery tools, and/or other tools (not shown), which can generate electrical pulses of a few kV. If such a tool gets close to the marker 40, the tool can cause a very large voltage across antenna wires 44 and destroy the switch 54.

To increase survivability of the marker 40 during operation of such tools, the ESD protection device 58 truncates voltage on the switch 58 device when the voltage approaches the maximal value. Generally, the ESD protection device 58 in the marker 40 should have low capacitance that does not shunt the antennas 44 for the frequency range of the small amplitude UWB signal coming from the signals from the probe 1020. In exemplary embodiments, the ESD protection device 58 may be a transient voltage suppressor, such as a Zener diode, a low-capacitance varistor, and the like.

Figure 4A:
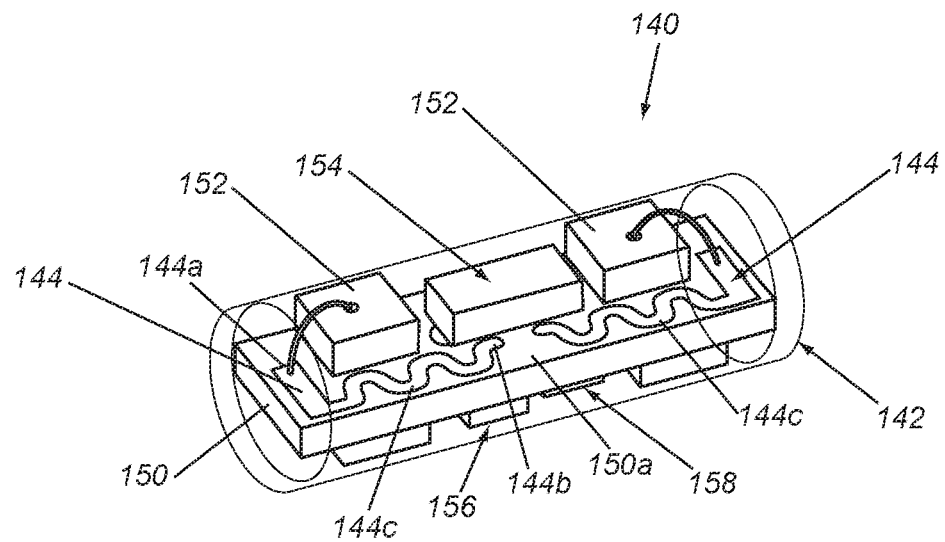
FIGS. 4A and 4B are perspective and top views, respectively, of another exemplary embodiment of a marker for implantation within a patient's body.
Figure 4B:
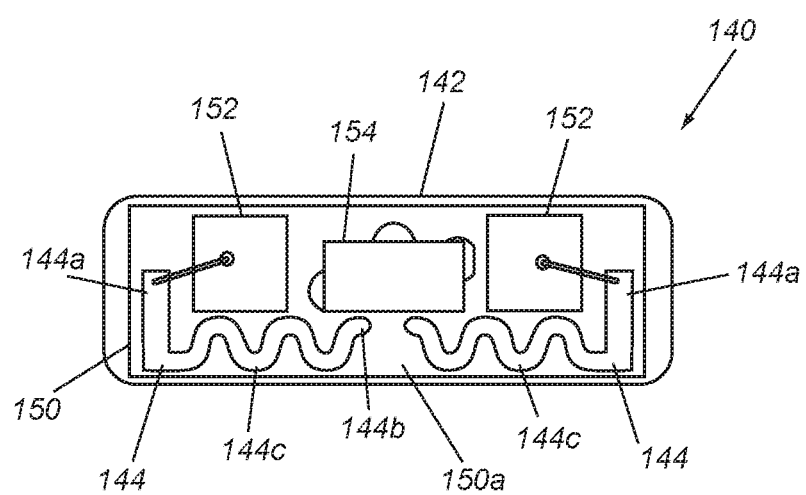

Turning to FIGS. 4A and 4B, an alternative embodiment of a reflector marker 140 is shown that includes an electronics package 142 carrying a circuit board or other substrate 150 including top and bottom (or first and second) surfaces, having one or more antennas 144 printed or otherwise formed directly thereon. As shown, the marker 140 also includes an energy converter, e.g., diodes 152, a switch, e.g., FET 154, coupled to the diodes 152, and an Electro Static Discharge (ESD) protection device 158 attached to one of the top and bottom surfaces, similar to other embodiments herein.

In addition, unlike the previous embodiments, the antennas 144 may be printed or otherwise formed directly on the top surface 150a of the substrate 150. Each antenna 144 may include a first end 144a coupled to the FET 154 and a second free end 144b. As shown, each antenna 144 includes a sinusoidal or other zigzag section 144c adjacent the free end 144b, e.g., to maximize an effective length or profile of the antenna 144 relative to the available surface on the substrate 151. In this embodiment, the antennas 144 may be coupled, respectively, to the drain and source of the FET 154, and the diodes 152 (in series) may be coupled between the gate and source, e.g., similar to the previous embodiments.

Figure 5A:
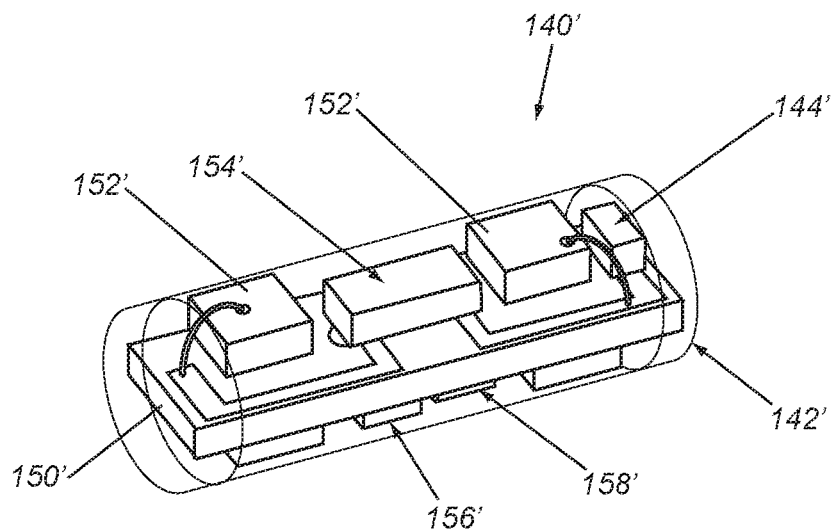
FIGS. 5A and 5B are perspective and top views, respectively, of yet another exemplary embodiment of a marker for implantation within a patient's body.
Figure 5B:
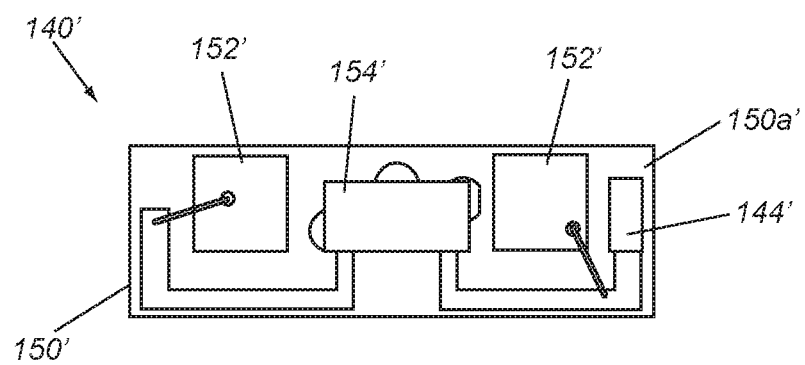

In a further alternative, shown in FIGS. 5A and 5B, the marker 140' may include one or more chip antennas 144' mounted to the substrate 151.' For example, as best seen in FIG. 5B, a single chip antenna 144' may be coupled to the drain of the FET 154,' and a capacitor (not shown) may be coupled across the drain and the source, e.g., in parallel with the ESD protection device 158.' Alternatively, a pair of chip antennas (not shown) may be provided coupled to the drain and source of the FET 154,' similar to the previous embodiments. In an exemplary embodiment, the chip antenna 144' may be a ceramic chip antenna, such as the Model W3078 manufactured by Pulse Electronics Corporation.

In still a further alternative, one of the antenna elements 44 or 144 may be replaced with a capacitor (not shown). For example, FIGS. 13A and 13B show an exemplary embodiment of a marker 40' similar to the marker 40 shown in FIGS. 1A-1C, i.e., including an electronics package 42' carrying a circuit board or other substrate 50' and including an energy converter, e.g., diodes 52,' a switch, e.g., FET 54,' coupled to the diodes 52,' and an Electro Static Discharge (ESD) protection device (not shown). Unlike the marker 40, the marker 40' includes a single antenna 44' coupled to the drain of the FET 54,' and a capacitor 59' coupled across the drain and the source, e.g., in parallel with the ESD protection device.

Returning to FIGS. 4A and 4B, the substrate 150 may be formed from one or more electrically insulating materials, e.g., a ceramic plate or board, having desired dielectric properties. The antennas 144 and/or other leads may be formed on the top and/or bottom surface of the substrate 150, e.g., by vapor deposition or other printing methods. As a result of the dielectric substrate 150, the antennas 144 may have a dielectric constant higher than air, which may make the marker 140 appear electrically larger than its actual physical size. It will be appreciated that the construction of the antennas 144 and substrate 150 may be modified to provide a complex impedance that may be changed to provide desired detection characteristics for the final marker 140, e.g., when being detected and/or located using the probe 1020.

Optionally, the marker 140 (or any of the other markers herein) may include a processor (not shown) coupled to the diodes 152 for identifying a code or message included in infrared signals transmitted to the marker 140. For example, the processor may be coupled between the diodes 152 and the gate of the FET 154 such that the FET 154 is only switched when a predetermined code is included in the incoming infrared signals. Thus, the processor may selectively provide a control signal to the gate to open and close the FET 154 when a set of infrared pulses are received by the diodes 152, e.g., to selectively apply a voltage across the drain and source of the FET. In an exemplary implementation, the code may include a sequence of infrared pulses with pulses separated in time and/or having different pulse lengths to provide a bit code that may be identified by the processor.

For example, with the FET 154 initially isolated from the diodes 152 (i.e., with the switch between the antennas 144 open), the processor may determine whether the pulses include a predetermined bit code assigned to the marker 140. If so, the processor may couple the diodes 152 to the FET 154 such that subsequent infrared pulses close and open the switch between the antennas 144, thereby modulating the reflective properties of the marker 140, as described elsewhere. Optionally, the processor may allow the FET 154 to continue to open and close until another predetermined bit code is identified, whereupon the processor may once again isolate the diodes 152 from the FET 154. Alternatively, the processor may activate the switching for a predetermined time and then open the FET 154 until reactivated.

In this manner, a plurality of markers (not shown) may be implanted within a patient's body that include respective processors assigned different bit codes. A probe, such as probe 1020 shown in FIGS. 6-9, may transmit infrared pulses that may be preceded by a desired bit code to activate and/or deactivate individual markers. For example, the probe may use a first code to activate, detect, and/or located a first marker and then, deactivate the first marker and use a second code to activate, detect, and/or locate a second marker, optionally repeating the cycle to assist a user in identifying a region within a patient's body within which multiple markers are implanted, as described further elsewhere herein.

Turning to FIGS. 6-9, an exemplary embodiment of a system 1010 is shown for localization of a target tissue region within a patient's body, such as a tumor, lesion, or other tissue structure within a breast 90 or other location within a body. As shown in FIG. 8, the system 1010 generally includes a delivery device 260 carrying one or more targets, tags, or markers 40 (one shown), a probe 1020 for detecting and/or locating the marker 40, e.g., using radar, e.g., ultra-wide band micro-impulse radar, narrow band continuous radar, and the like, and a controller and/or display unit 1040 coupled to the probe 1020, e.g., using one or more cables 1036, similar to embodiments described in the applications incorporated by reference herein.

For example, the probe 1020 may be a portable device having electromagnetic signal emitting and receiving capabilities, e.g., a micro-power impulse radar (MIR) probe, similar to embodiments described in the applications incorporated by reference herein. As shown in FIG. 6, the probe 1020 may be a handheld device including a first or distal end 1024 intended to be placed against or adjacent tissue, e.g., a patient's skin or underlying tissue, and a second or proximal end 1022, e.g., which may be held by a user. Generally, the probe 1020 includes one or more antennas, e.g., a transmit antenna and a receive antenna (not shown) mounted on a ceramic disk 1032 (shown in FIG. 7), e.g., to provide an interface between the antennas and contacted tissue. In addition, the probe 1020 includes a light transmitter, e.g., a plurality of light fibers 1038 (shown in FIG. 7), LEDs (not shown), and the like, configured to transmit light pulses (represented by dashed lines 1038a in FIG. 6) into tissue contacted by the distal end 1024, e.g., into breast tissue 90, as shown in FIG. 6. The light fibers 1038 may be coupled to a light source, e.g., LEDs (not shown) within the probe 1020 or display unit 1040, e.g., by coupling 1039, such that light from the light source passes through the light fibers 1038 distally from the distal end 1024 of the probe 1020.

In an exemplary embodiment, the light source is an infrared light source, e.g., capable of delivering near infrared light between, for example, eight hundred and nine hundred fifty nanometers (800-950 nm) wavelength. Optionally, the light fibers may include one or lenses, filters, and the like (not shown), if desired, for example, to focus the light transmitted by the probe 1020 in a desired manner, e.g., in a relatively narrow beam extending substantially parallel to the central axis of the probe 1020, in a wider beam, and the like.

Optionally, the light source may be capable of transmitting relatively narrow bandwidths within the infrared spectrum, e.g., to activate individual markers including coatings and/or filters that limit activation of the respective markers based on respective narrow bandwidths. For example, the light source may include a plurality of LEDs, each capable of transmitting a relatively narrow and distinct bandwidth than the others. Alternatively, the light source may transmit a broad bandwidth of infrared (or other broader spectrum) light, and the probe 1020 may include a plurality of filters or other components (not shown) that limit the portion of the bandwidth that is transmitted by the probe 1020. In this manner, pulses of narrow band infrared light may be transmitted by the probe 1020 to activate individual markers, as described elsewhere herein.

Alternatively, the probe 1020 may include other energy sources instead of the light transmitter 1038. For example, a source of electromagnetic energy, radiofrequency (RF) energy, vibrational energy, and the like (not shown) may be provided on the distal end 1024 of the probe 1020 for delivering energy pulses to activate the marker 40, as described elsewhere herein. The energy source(s) may be pulsed in a predetermined manner, e.g., to cause the circuits of the marker 40 to be alternately activated and deactivated.

The probe 1020 may include a processor within the display unit 1040 including one or more controllers, circuits, signal generators, gates, and the like (not shown) needed to generate signals for transmission by the transmit antenna and/or to process signals received from the receive antenna. The components of the processor may include discrete components, solid state devices, programmable devices, software components, and the like, as desired. For example, the probe 1020 may include an impulse generator, e.g., a pulse generator and/or pseudo noise generator (not shown), coupled to the transmit antenna to generate transmit signals, and an impulse receiver for receiving signals detected by the receive antenna. The processor may include a micro-controller and a range gate control that alternately activate the impulse generator and impulse receiver to transmit electromagnetic pulses, waves, or other signals via the transmit antenna, and then receive any reflected electromagnetic signals via the receive antenna, e.g., similar to other embodiments herein. Exemplary signals that may be used include microwave, radio waves, such as micro-impulse radar signals, e.g., in the ultralow bandwidth region.

The probe 1020 may be coupled to a display 1042 of the display unit 1040, e.g., by cables 1036, for displaying information to a user of the probe 1020, e.g., spatial or image data obtained via the antennas. Optionally, the probe 1020 may include other features or components, such as one or more user interfaces, memory, transmitters, receivers, connectors, cables, power sources, and the like (not shown). For example, the probe 1020 may include one or more batteries or other internal power sources for operating the components of the probe 1020. Alternatively, the probe 1020 may include a cable, such as one of the cables 1036, that may be coupled to an external power source, e.g., standard AC power, for operating the components of the probe 1020.

As shown in FIG. 6, the internal components of the probe 1020 may be provided in a housing or casing such that the probe 1020 is self-contained. For example, the casing may be relatively small and portable, e.g., such that the entire probe 1020 may be held in a user's hand. Optionally, a portion of the probe 1020 may be disposable, e.g., a portion adjacent the distal end 1024, or a disposable cover, sleeve, and the like (not shown) may be provided if desired, such that at least a proximal portion of the probe 1020 may be reusable, e.g., similar to embodiments described in the applications incorporated by reference herein. Alternatively, the entire probe 1020 may be a disposable, single-use device while the display unit 1040 may be used during multiple procedures by connecting a new probe 1020 to the display unit 1040, which may remain out of the surgical field yet remain accessible and/or visible, as desired. Additional information on construction and/or operation of the probe 1020 may be found in the applications incorporated by reference elsewhere herein.

Figure 9:
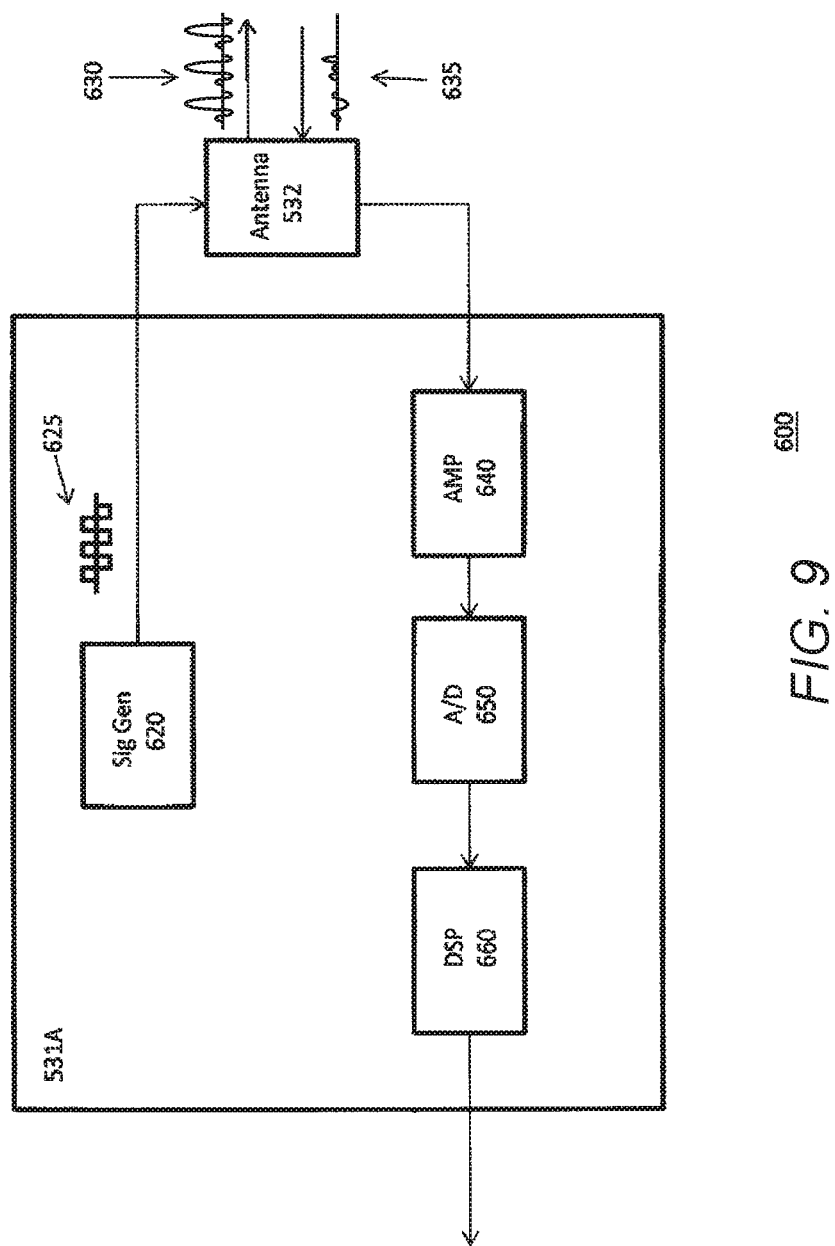
FIG. 9 is block diagram depicting exemplary components of the probe of FIG. 8.

FIG. 9 is a block diagram 600 showing exemplary components of the probe 1020 (although, alternatively, some of the components may be located within the display unit 1040 of FIG. 8). The probe 1020 may include a signal generator 620, an amplifier 640, an analog-to-digital (A/D) converter 650, and a digital signal processor (DSP) 660. The signal generator 620, e.g., a reference oscillator, produces an oscillating signal, such as a square wave signal, a triangular wave signal, or a sinusoidal signal.

For example, a square wave signal 625 may be sent from the signal generator 620 to the transmit antenna of the antenna portion 532 of the probe 1020. When the square wave signal 625 passes through the transmit antenna, the transmit antenna acts as a band pass filter ("BPF") and converts the square wave signal 625 to a series of pulses 630. As such, the transmit signal 1034T (shown in FIG. 6) transmitted by the probe 1020 includes a series of pulses 630. The transmit signals 1034T may be transmitted into the tissue and reflected from the marker 40 (as shown in FIG. 6), as represented by the receive signals 1034R. Once the transmit signal 1034T is reflected from the marker 40, the reflected signal (i.e., the receive signals 1034R) includes a series of attenuated pulses 635 (shown in FIG. 9).

The receive antenna of the antenna portion 532 of the probe 1020 may receive the receive signals 1034R (shown in FIG. 6). As shown in FIG. 9, the receive signals 1034R, which may include a series of attenuated pulses 635, may be inputted into an amplifier 640 in order to amplify the gain of the pulses 635. The output of the amplifier 640 may be inputted into an A/D converter 650 in order to convert the amplified analog signal into a digital signal. The digital signal output from the A/D converter 650 may be inputted into a DSP 660 for processing. The DSP 660 may perform a number of processing functions including, but not limited to, calculating a difference in time from the time the transmit signal 501 was sent to the time the receive signal 502 was received, determining the distance from the tip of the microwave antenna probe 531 to the marker 521, determining the location of the marker 40 in relation to the tip of the probe 1020, measuring the amplitude of the receive signals 1034R, and/or determining the direction the marker 40 is located in relation to the tip of the probe 1020, e.g., as described in the applications incorporated by reference herein. The output of the DSP 660 may be presented on the display 1042 of the display unit 1040.

Turning to FIGS. 10A-10D, an exemplary embodiment of an antenna probe 930 is shown that may be used in any of the systems and methods described elsewhere herein. Generally, the probe 930 includes a housing 940, an antenna subassembly 950, and shielding 980. Optionally, the probe 930 may include an outer sleeve or cover (not shown) surrounding one or more components of the probe 930, e.g., surrounding openings in the housing 940, for reducing contamination, exposure, and/or otherwise protecting the internal components of the probe 930.

Figure 11:
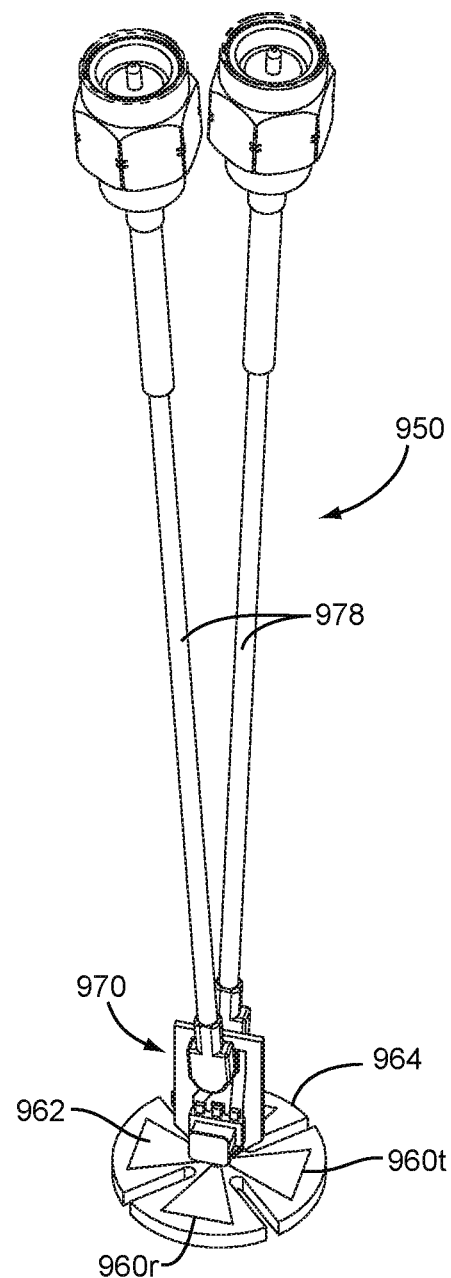
FIG. 11 is a perspective view of an antenna subassembly that may be included in the probe of FIG. 10A.
Figures 12A, 12B, 12C:
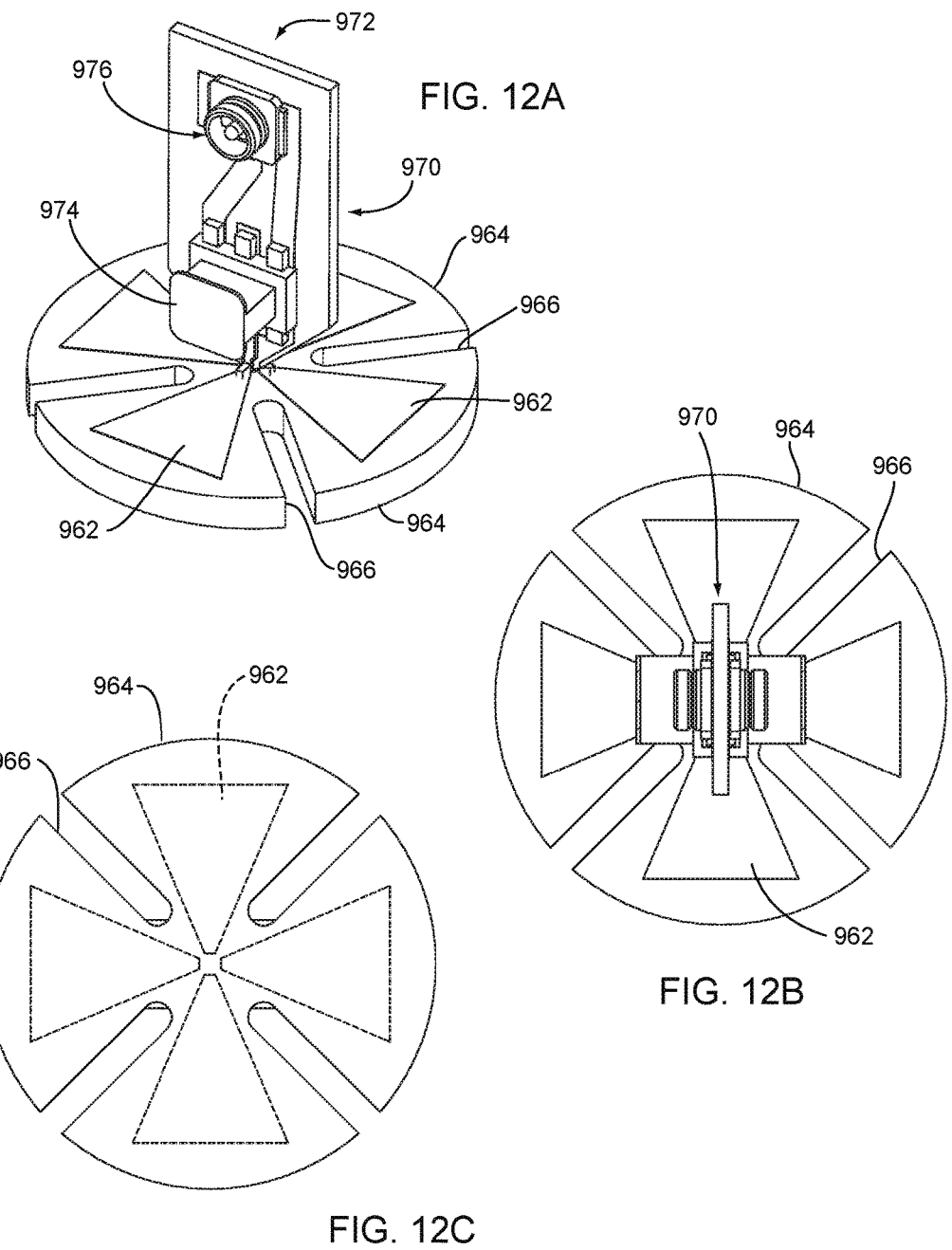
FIGS. 12A-12C are perspective, top, and bottom views, respectively, of the antenna elements of the antenna subassembly of FIG. 11.

With additional reference to FIG. 11, the antenna subassembly 950 includes a transmit antenna 960t and a receive antenna 960r, each having a bowtie configuration, combined to form a Maltese cross antenna. As shown in FIGS. 12A-12C, each antenna 960 includes a pair of antenna elements 962 offset ninety degrees (90°) from one another on a disk or other base of dielectric material 964. Each of the antenna elements 962 may be formed separately and then attached to the disk 964 or may be deposited directly onto the disk 964. In an exemplary embodiment, the antenna elements 962 may be formed from silver film or other material deposited onto the top surface of ceramic disk 964.

Circuitry 970 may be coupled to the antennas 960, e.g., including a PCB 972 on which are provided one or more transformers 974 and connectors 976 coupled to the respective antenna elements 962 by appropriate leads. Coaxial cables 978 may be coupled to the connectors 976 to allow the antennas 960 to be coupled to other components of the system, similar to other embodiments described elsewhere herein.

As best seen in FIG. 12A-12C, the disk 964 includes a plurality of radial slots 966 between the antenna elements 962. Thus, the antenna elements 962 may be substantially isolated from one another by air within the slots 966, which may increase sensitivity, reduce crosstalk and/or other noise, and the like. Alternatively, the slots 966 may be filled with other insulating material, e.g., foam and the like (not shown), which may have a desired relatively low dielectric constant to substantially isolate the antenna elements 962 from one another.

Figures 10A, 10B:
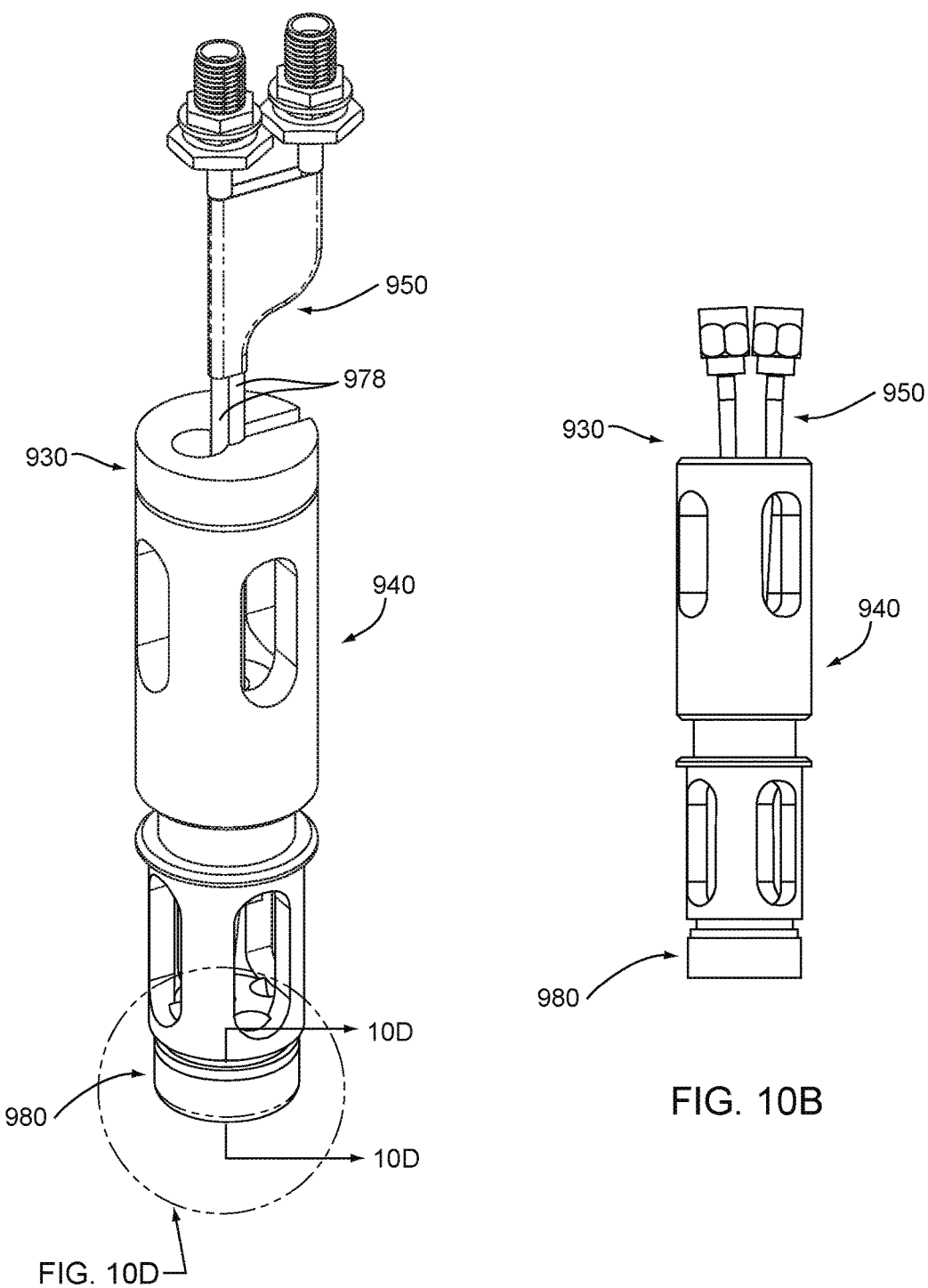
FIGS. 10A and 10B are perspective and side views, respectively, of another exemplary of an antenna probe that may be included in a system such that shown in FIGS. 7-9.
Figures 10C, 10D:
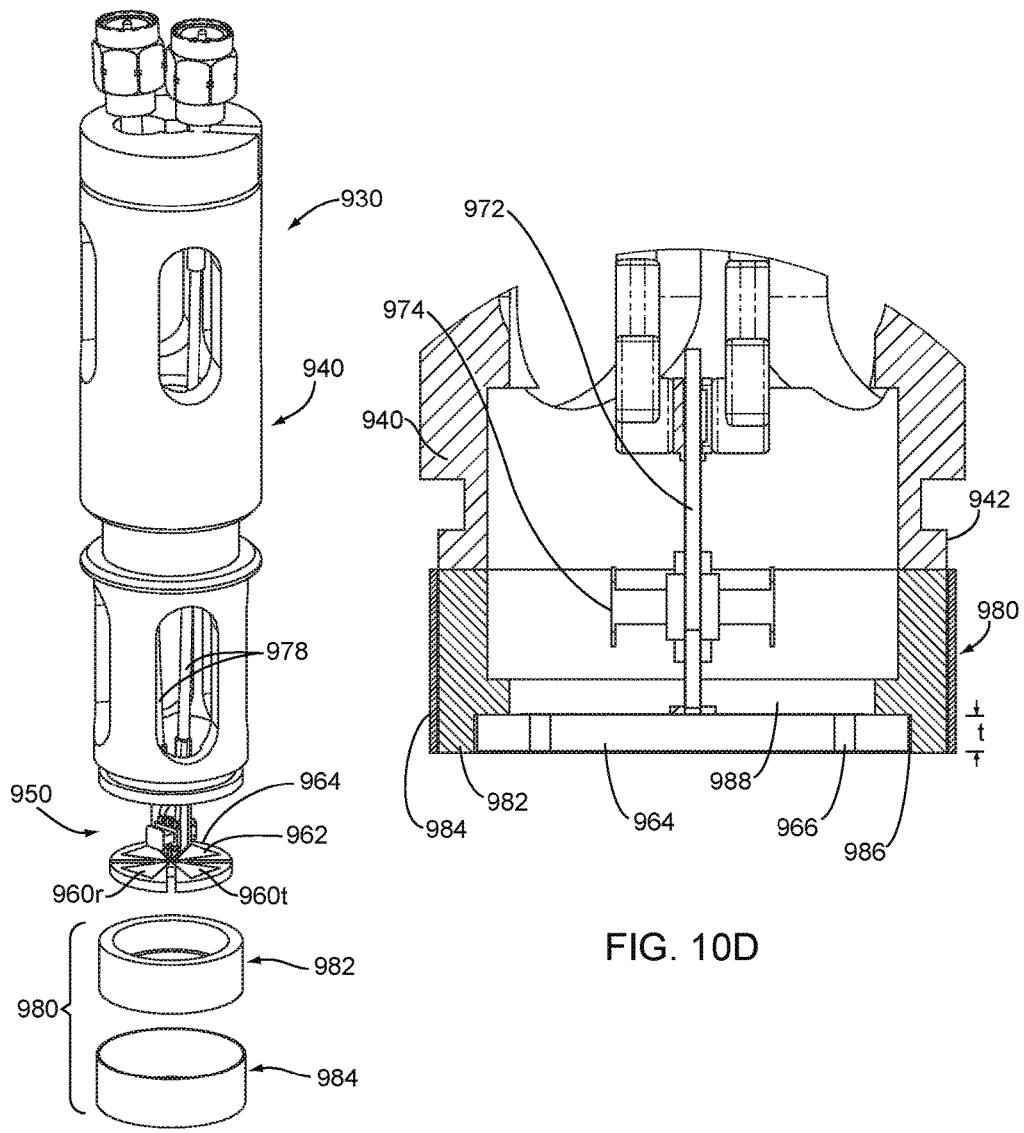
FIG. 10C is a partially exploded view of the probe of FIG. 10A.
FIG. 10D is a cross-section of the tip of the probe of FIG. 10A taken along line 10D-10D.

As best seen in FIG. 10D, the disk 964 may be mounted within the shielding 980, which may in turn, be coupled to the tip 942 of the housing 940, e.g., by one or more of bonding with adhesive, sonic welding, fusing, cooperating connectors (not shown), and the like. As shown, the shielding 980 includes an inner insulation layer, e.g., formed from a collar of nylon or other polymeric material, surrounded by a relatively thin outer shield 984, e.g., formed from copper or other material, to provide a Faraday shield. In an exemplary embodiment, a layer of copper tape may be wrapped around the inner shield 982 with the ends secured together. Alternatively, the outer shield 984 may be a sleeve of shielding material into which the inner shield 982 is inserted and attached, e.g., by bonding with adhesive, interference fit, and the like.

As shown in FIG. 10D, the shielding 980 may have a length substantially greater than the thickness "t" of the disk 964. For example, the inner shield 982 may include an annular recess 986 into which the disk 964 may be inserted and attached, e.g., by interference fit, bonding with adhesive, and the like. As shown, the bottom surface of the disk 964 may be substantially flush with the distal end of the shielding 980 such that the disk 964 may provide an interface to contact tissue during use, as described elsewhere herein. Optionally, a Mylar film or other relatively thin layer of material (not shown) may be provided over the bottom surface of the disk 964 and/or the shielding 980, e.g., to prevent fluids or other material entering the tip, reduce contamination, and/or otherwise protect the tip of the probe 930.

With continued reference to FIG. 10D, the top surface of the disk 964 (with the antenna elements 962, not shown, thereon) may be exposed to a region of air within the shielding 980. Because of the low dielectric constant of air, the transmission from the transmit antenna 960*t* is focused distally, i.e., towards the tissue contacted by the disk 964. With the material of the disk 964 chosen to substantially match the dielectric constant of tissue, the depth of transmission into the tissue may be enhanced. The air behind the disk 964 may minimize lost energy that would otherwise be emitted by the transmit antenna 960*t* away from the tissue. Similarly, the disk 964 may focus the sensitivity of the receive antenna 960*r* directed towards the tissue. The air behind the disk 964 within the shielding 980 (as well as the slots 966 between the antenna elements 962) may minimize crosstalk, noise and/or may otherwise enhance operation of the probe 930. Additional information regarding the probe 930 and/or alternative embodiments may be found in the applications incorporated by reference herein.

The system 1010 of FIG. 6 may be used during a medical procedure, for example, in a breast biopsy or lumpectomy procedure, e.g., to facilitate localization of a lesion or other target tissue region and/or to facilitate dissection and/or removal of a specimen from a breast 90 or other body structure. It should be noted that, although the system 1010 is described as being particularly useful in localization of breast lesions, the system 1010 may also be used in localization of other objects in other areas of the body, e.g., as described in the applications incorporated by reference herein.

Before the procedure, a target tissue region, e.g., a tumor or other lesion, may be identified using conventional methods. For example, a lesion (not shown) within a breast 90 may be identified, e.g., using mammography and/or other imaging, and a decision may be made to remove the lesion. A marker 40 (which may be any of the embodiments described herein) may be implanted within the breast 90 within or adjacent the target lesion, e.g., using a needle or other delivery device, such as the delivery device 260 shown in FIG. 8.

Once the marker(s) 40 is implanted, as shown in FIG. 6, the probe 1020 may be placed against a patient's skin, e.g., against the breast 90. Signals from the antenna of the probe 1020 may be delivered along with pulsed light from the light source to cause the switch 54 to open and close as the marker 40 receives and reflects the signals back to the probe 1020. If there is substantial clutter, crosstalk, or other noise being received by the probe 1020, e.g., due to the probe antennas, tissue or other structures within the patient's body near the marker 40, and the like, the reflected signals from the two states (switch 54 open and closed) may be subtracted from one another, substantially eliminated the other noise, and allowing the probe 1020 to identify and/or locate the marker 40.

Thus, the probe 1020 may use the modulated reflected signals to increase the signal-to-noise ratio of the signals. For example, the modulation of the marker 40 may modify the impedance of the marker 40 and/or the tissue within which the marker 40 is implanted. In particular, the antennas 144, 144' mounted on a ceramic substrate 150, 150' may modify the effective impedance of the tissue contacting or immediately surrounding the marker 140, 140' such that the probe 1020, using subtraction, may easily detect and/or locate the marker 140, 140' based on the changes in the impedance. Thus, the antennas 144, 144' may not behave as actual antennas but probes that allow modulation of the adjacent tissue.

Returning to FIG. 8, the display 1042 may display information to the user to facilitate locating the marker 40 within the breast 90. For example, the display 1042 may simply be a readout providing distance, angle, orientation, and/or other data based on predetermined criteria, e.g., based on the relative distance from the marker 40 to the probe 1020. The distance information may be displayed as a numerical value representing the distance in units of length, such as in inches (in.) or centimeters (cm). In addition or alternatively, a speaker 1044 on the display unit 1040 may produce an audible indication of distance, e.g., spaced-pulses that increase in speed as the probe 1020 is closer to the marker 40. In another alternative, the display 1042 may present a graphical image (e.g., a two-dimensional or three-dimensional image) depicting the marker 40, the probe 1020, the distance from the probe 1020 to the marker 40, and/or a physiological picture of the body part containing the marker (e.g., the breast).

For example, as shown in FIG. 6, the distal end 1024 of the probe 1020 may be placed adjacent or in contact with the patient's skin, e.g., generally above the lesion, and/or otherwise aimed generally towards the lesion and marker 40, and activated. The transmit antenna (not shown) of the probe 1020 may emit transmit signals 1034T that travel through the tissue and are reflected off of the marker 40. Return signals 1034R may be reflected back to the receive antenna (not shown) in the probe 1020, which may then determine a spatial relationship between the marker 40 and the distal end 1024 of the probe 1020, e.g., a distance and/or orientation angle, to facilitate determining a proper direction of dissection for the surgeon.

In addition, substantially simultaneously, the probe 1020 may transmit light pulses 1038a, which may be received by the diodes 52 of the marker 40 (not shown, see, e.g., FIGS. 3A and 3B). The diodes 52 may alternately generate a voltage, causing the switch 54 to open and close. This causes the marker 40 to change the phase of and/or otherwise modulate the signals reflected back to the probe 1020, which may process the signals, e.g., by subtraction, to identify and/or locate the marker 40, and consequently the target lesion.

In one embodiment, the processor for the probe 1020 may perform localization in two steps, namely an initial detection step to identify the marker 40, and a range detection step to determine the distance from the probe 1020 to the marker 40. For example, in the detection step, the processor may simply use the amplitude of the return signals to identify the marker 40. Once the marker 40 has been identified, the processor may be use time delay to determine the distance from the probe 1020 to the marker 40. For example, the time delay between the time the transmit signal 1034T is transmitted by the transmit antenna and the time the return signal 1034R is received by the receive antenna may be directly proportional to the distance from the probe 1020 to the marker 40, and the processor may determine the distance based on this time delay and present it to the user.

Tissue may then be dissected, e.g., by creating an incision in the patient's skin and dissecting intervening tissue to a desired depth, e.g., corresponding to a target margin around the lesion is reached. A tissue specimen may be excised or otherwise removed using conventional lumpectomy procedures, e.g., with the marker 40 remaining within the removed specimen 1046.

Optionally, the system shown in FIG. 8 may be used to detect and/or locate multiple markers implanted together within a tissue region. For example, a plurality of markers (not shown) may be implanted within a breast 90 spaced apart around a lesion, e.g., to define a desired margin for a lumpectomy. The probe 1020 may be used to activate each of the markers, e.g., in a predetermined sequence or other procedure, such that information may be provided regarding each of the markers.

For example, as described above, each marker may be activated by a different relatively narrow bandwidth of infrared light, and the probe 1020 may transmit infrared pulses sequentially in each of the different bandwidths to activate, detect, and/or locate the markers. For example, while transmitting MIR pulses, the probe 1020 may transmit a first bandwidth to activate and detect a first marker, and thereafter transmit a second bandwidth to activate and detect a second marker, e.g., repeating the cycle in a desired manner to provide information regarding the locations of the markers. Alternatively, the probe 1020 may include codes in the infrared pulses, e.g., to activate and/or deactivate individual markers such only an activated marker opens and closes the switch to modulate radar signals from the probe 1020. Thus, when the probe 1020 subtracts the received modulated signals, the inactive markers produce no detectable response while the activated marker modulates the radar signals reflected back to the probe 1020.

In still another alternative, the characteristics of the individual markers may be set such that individual markers reflect only radar signals of a predetermined frequency range. For example, the materials and/or other properties of the antennas and/or substrates of the markers may be different, e.g., to provide different impedance characteristics that respond to different frequencies of radar signals This, in this alternative, the probe 1020 may transmit radar signals at a first frequency to activate and detect a first marker, and thereafter transmit radar signals at a second different frequency to activate and detect a second marker, repeating the cycle, as desired to locate all of the markers.

Figure 14:
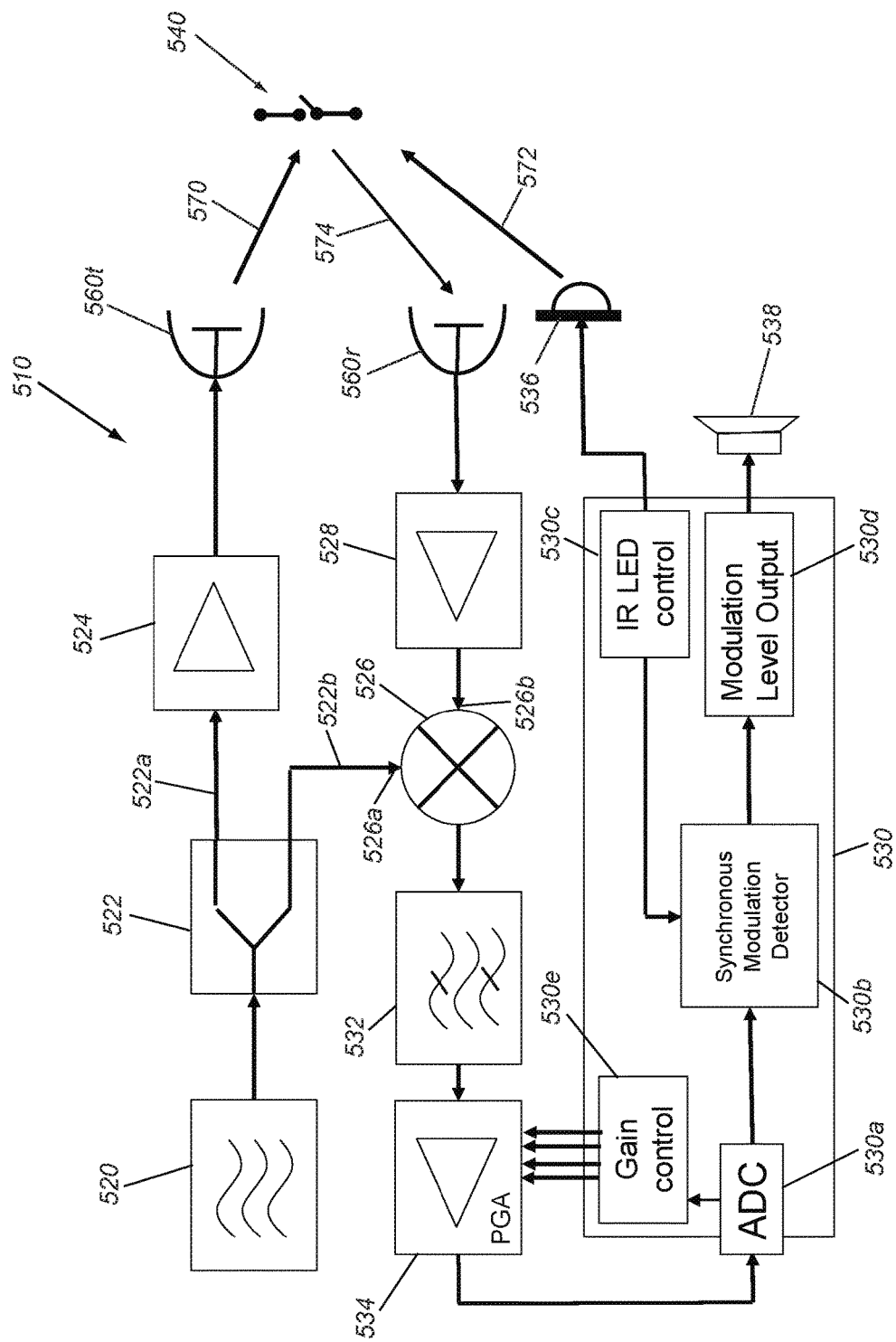
FIG. 14 is a schematic representation of components of another exemplary embodiment of a system for identifying and/or locating a marker implanted within a patient's body.
Figure 15:
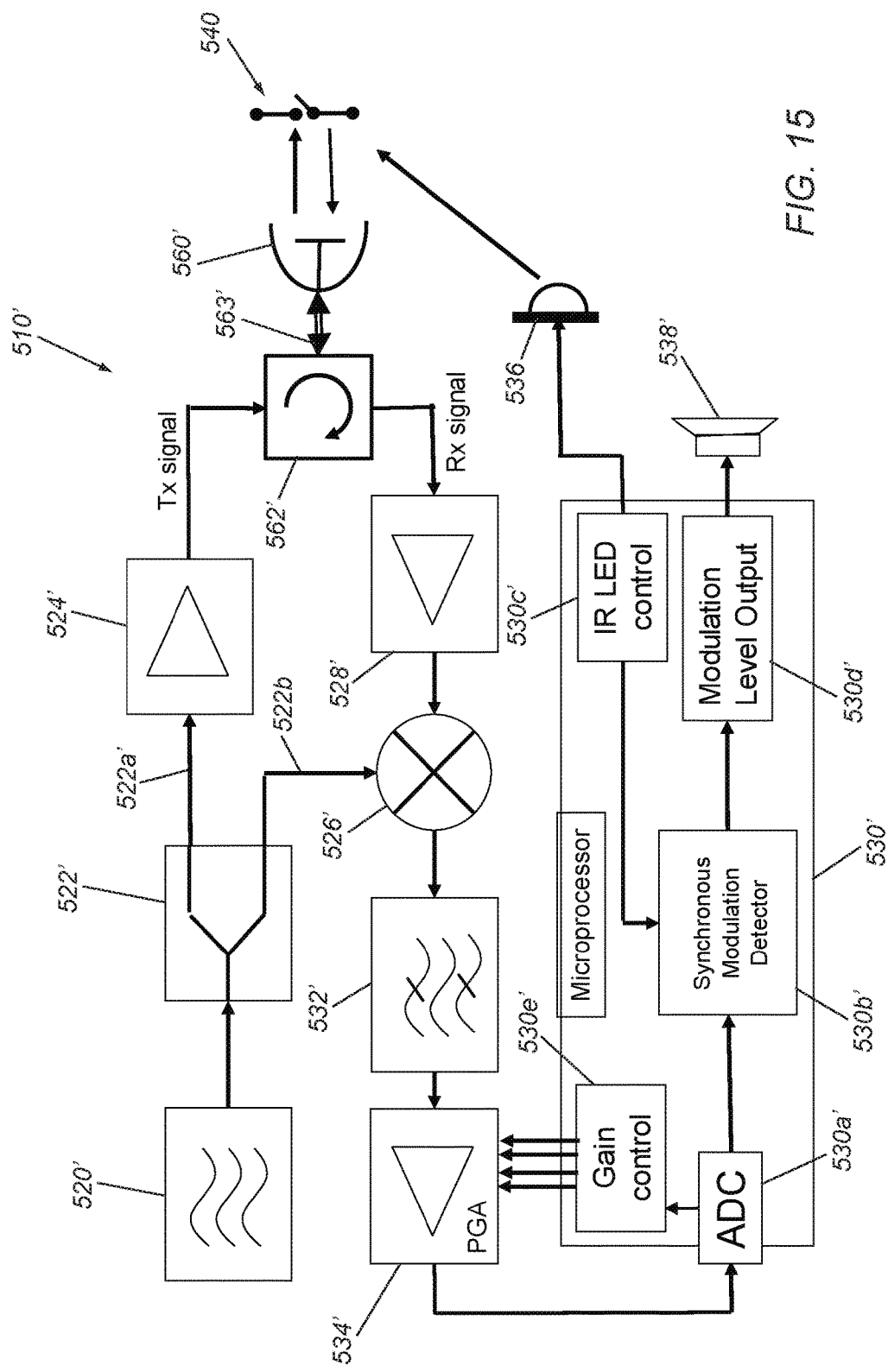
FIG. 15 is a schematic representation of components of yet another exemplary embodiment of a system for identifying and/or locating a marker implanted within a patient's body.

Turning to FIG. 14, a schematic of another exemplary embodiment of a system 510 is shown for identifying and/or detecting a marker 540 implanted within tissue (not shown). Generally, the system 510 includes one or more antennas, e.g., a transmit antenna 560t and a receive antenna 560r, and a light source, e.g., one or more infrared (IR) LEDs 536, carried on a distal tip of a probe (not shown), and a processing and/or display unit (also not shown), e.g., similar to the probe and display unit shown in FIGS. 6-8 and other embodiments described elsewhere herein and in the applications incorporated by reference herein. Alternatively, as shown in FIG. 15, the system 510' may include a single antenna 560' and a circulator 562' that controls transmission and reception of signals via the antenna 560,' as described further elsewhere herein.

Figure 16:
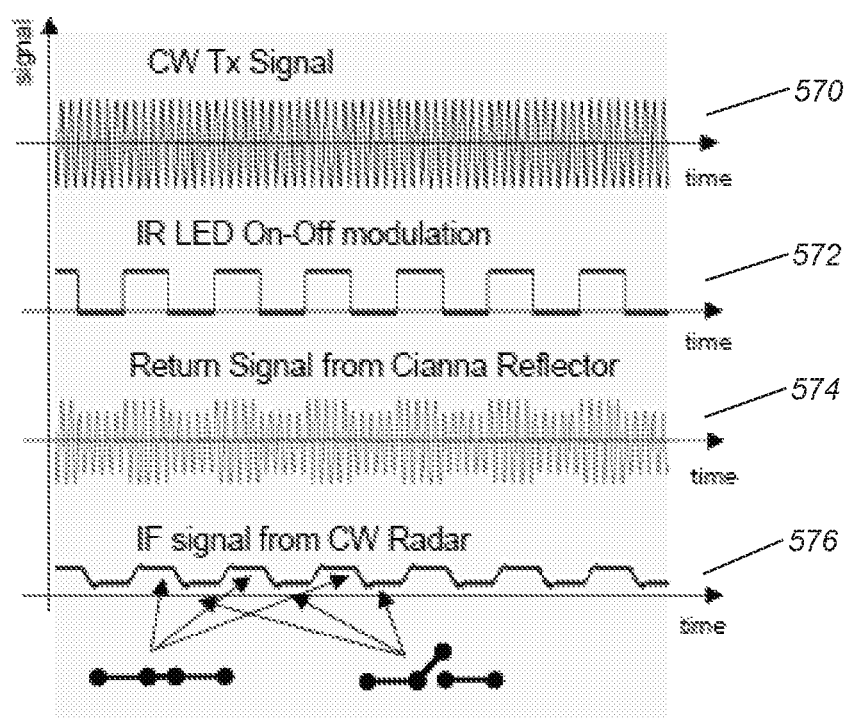
FIG. 16 is a graph showing exemplary signals that may be transmitted and received by a system, such as those of FIGS. 14 and 15 to identify a marker implanted within a patient's body.

Unlike the previous embodiments, as shown in FIG. 16, when activated, the probe of the system 510 (or 510') may transmit a substantially continuous, e.g., sinusoidal, radio frequency or microwave signal 570 via the transmit antenna 560t (or antenna 560'). Rather than a broadband microimpulse radar signal, the signal 570 may be a narrow band signal, e.g., having a frequency between about 300 MHz and 300 GHz, or between about 300 MHz and 1 GHz. In synchronization with the RF signal 570, light pulses 572 are transmitted via the LED(s) 536, thereby generating a return RF signal 574 that is reflected off of the marker 540 and modulated by the infrared pulses 572. As shown in FIG. 14, the system 510 may include one or more controllers, processors, circuits, signal generators, gates, and/or other components that generate the signals 570, 572 transmitted by the transmit antenna 560t and LED(s) 536, and/or that process the return signal 574 received from the receive antenna 560r, e.g., as represented by IF signal 576 shown in FIG. 16 and described further below. The components of the system 510 may include discrete components, solid state devices, programmable devices, software components, and the like, which may be distributed between the probe and display unit, as desired.

For example, with continued reference to FIG. 14, the system 510 may include a wave generator 520, e.g., generating a continuous radio frequency or microwave sinewave signal at a desired frequency, that is split by power divider 522 such that a first signal 522a is delivered through an amplifier 524 to the transmit antenna 560t, which transmits signal 570 (e.g., signal 570 shown in FIG. 16), and a second signal 522b is delivered to a first input 526a of a mixer 526. In addition, the mixer 526 receives return signal 574 (e.g., signal 574 shown in FIG. 16) from the return antenna 560r at a second input 526b via another amplifier 528, and produces an intermediate frequency (IF) signal (e.g., signal 576 shown in FIG. 16) that contains components associated with the modulation of the amplitude and phase of the return signal 572. For example, the mixer 526 may remove the high frequency, RF, components in the return signal 572 to produce a signal, e.g., signal 576, that includes only relatively low frequency components resulting from the modulation caused by the infrared pulses.

In particular, similar to other embodiments herein, the IR light from the LED(s) 536 causes the marker 540 to alternate between two form factors, e.g., opening and closing a switch (not shown) coupled to antennas of the marker 540 to modulate the reflective properties of the marker 540 and/or surrounding tissue, e.g., similar to the configurations shown in FIGS. 3A and 3B. For example, FIG. 16 shows the alternating configuration of the marker antennas and the regions of the IF signal 576 corresponding to the two configurations. Because other reflections in the return signal 574 do not depend on the IR light modulation, they remain unchanged and can be removed from the IF signal 576, e.g., by subtraction of portions of the signals corresponding to the two reflective states of the marker 540.

The system 510 includes one or more processors, e.g., microprocessor 530, that may control the various components and process the IF signal from the mixer 526, e.g., after being filtered and amplified by a band-pass filter 532 and amplifier 534, e.g., a programmable gain amplifier (PGA). For example, as shown in FIG. 14, the microprocessor 530 may include an analog-to-digital converter (ADC) 530a coupled to a synchronous modulation detector 530b, which, in turn, is coupled to an IR controller 530c and an output controller 530d. The IF signal from the mixer 526 may be applied to the BP filter 532, which is tuned to the frequency of the LED switching amplified by the PGA 534 controlled by the microprocessor 530, e.g., by gain controller 530e. The filtered and amplified signal is then digitized at the ADC 530a (or alternatively, using an external ADC, not shown), and processed using the synchronous modulation detector 530b, which evaluates the amplitude of the synchronously switching components in the return signal 572 from the return antenna 560r. The values of the computed amplitude at the detector 530b may be output to the user, e.g., via output controller 530d to one or more output devices 538 as an indicator of the location and/or distance from the probe to the marker 540.

Due to propagation losses, the strength of the return signal 574 is inversely proportional to the range from the antennas 560 to the marker 540. Thus, the resulting amplitude determined by the detector 540b is inversely proportional to the distance from the probe to the marker 540, and may be used to indicate relative distance from the probe to the marker 540 as the probe is moved around over the tissue region within which the marker 540 is implanted, e.g., similar to other embodiments herein and in the applications incorporated by reference herein. For example, in one embodiment, the output device 538 may be a speaker that produces a clicking or other pulsed output that increases in pulse rate as the computed amplitude increases, thereby indicating that the probe is closer to the marker 540, e.g., to identify the shortest path from the patient's skin to the target tissue region. In addition or alternatively, the output device 538 may include a display, which may include a numerical value, bar, or other visual output indicating the strength of the computed amplitude and, consequently, the relative distance from the probe to the marker 540.

The system 510' shown in FIG. 15 generally operates in a similar to manner to the system 510. However, in this embodiment, the probe only includes a single antenna 560 that both transmits and receives signals. To accomplish this, the system 510' includes a circulator circuit 562' including an in/out terminal 563' connected to the antenna 560.' For example, the transmit signal 522a' from the signal generator 520' may be directed to an input of the circulator 562,' after amplification by amplifier 524,' and the circulator 562' directs the signal to the in/out terminal 563' such that the antenna 560' transmits the signal 570 towards the marker 540. The return signal 574 is received by the antenna 560' and in/out terminal 563' and is redirected by the circulator 562' to an output of the circulator 562' coupled to the amplifier 528' and mixer 526.' The mixer 526,' microprocessor 530,' and other components then process the return signal, similar to the previous embodiment, to provide an output indicating the range from the probe to the marker 540.

Figure 17:
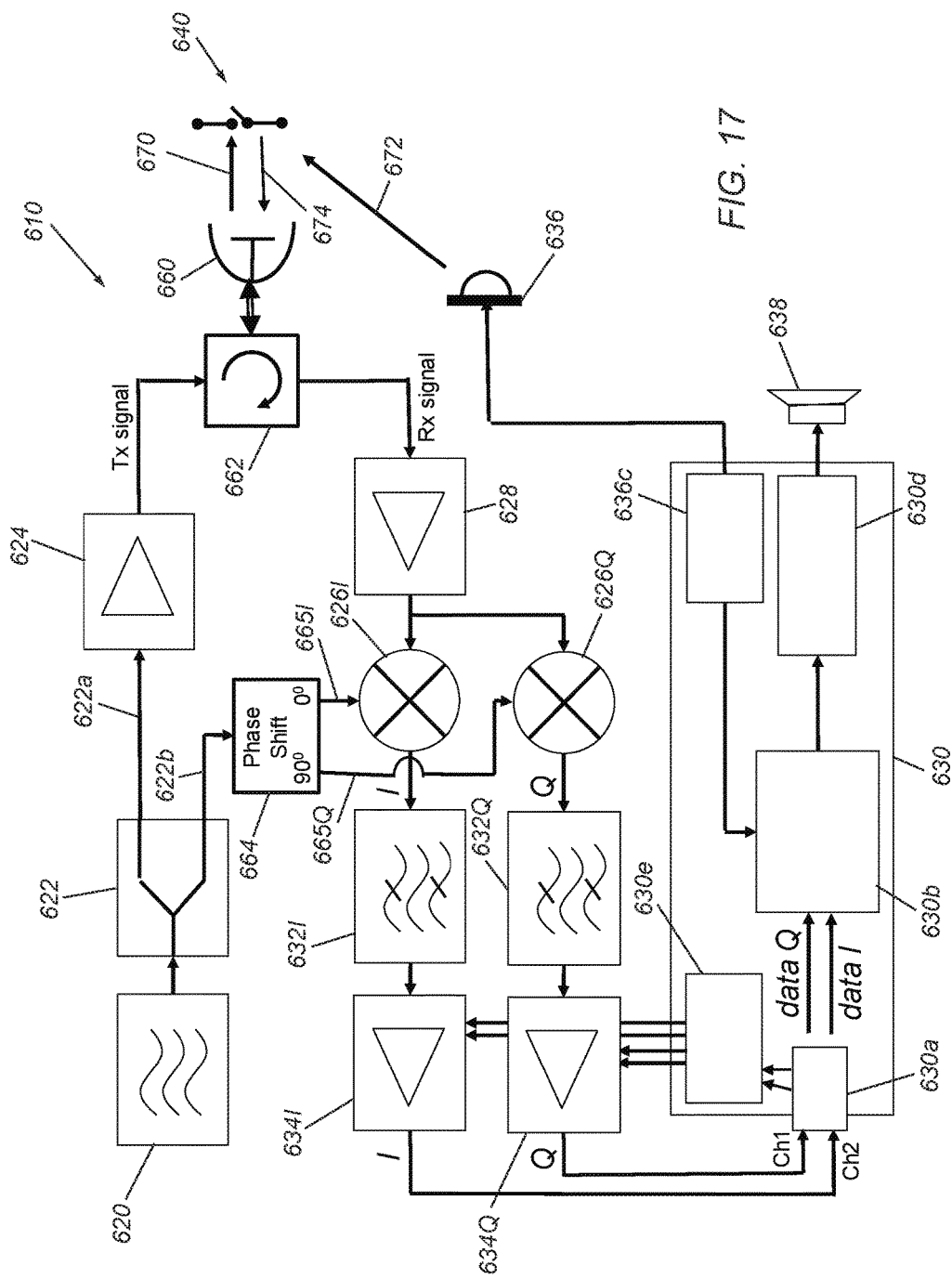
FIG. 17 is a schematic representation of components of still another exemplary embodiment of a system for detecting and locating a marker implanted within a patient's body.

Turning to FIG. 17, a schematic of yet another exemplary system 610 is shown for identifying and/or detecting a marker 540 (which may be any of the embodiments herein) implanted within tissue (not shown). Generally, the system 610 includes a probe (not shown) including one or more antennas, e.g., a single transmit/receive antenna 660 coupled to a circulator circuit 662 (or alternatively separate transmit and receive antennas, not shown), and a light source, e.g., one or more infrared (IR) LEDs 636, carried on or within a distal tip thereof, and a processing and/or display unit (also not shown), e.g., similar to other embodiments herein. For example, similar to the previous embodiments, the system 610 may include a wave generator 620, e.g., generating a continuous radio frequency or microwave sinewave signal at a desired frequency, that is split by power divider 622 into first and second signals 622a, 622b, with the first signal 622a delivered through an amplifier 624 to the antenna 660, which transmits radar transmit signal 670 (e.g., similar to signal 570 shown in FIG. 16).

Unlike the previous embodiments, the system 610 utilizes quadrature detection to enable evaluation of changes in amplitude and phase of radar signals separately to locate and/or determine distance to the marker 540. For example, to provide quadrature detection, the system 610 may include a quadrature phase splitter 664 that receives the second signal 622b from the divider 622 and is coupled to mixers 626I, 626Q. The phase splitter 664 delivers an input signal 665I to the first mixer 626I that is the same as the second signal 622b and creates a ninety degree) (90°) shifted replica 665Q that is delivered to the second mixer 626Q. The mixers 626I, 626Q also each receive return signal 674 (e.g., similar to signal 574 shown in FIG. 16) from the antenna 660 and circulator 662, e.g., via another amplifier 628.

Figure 18:
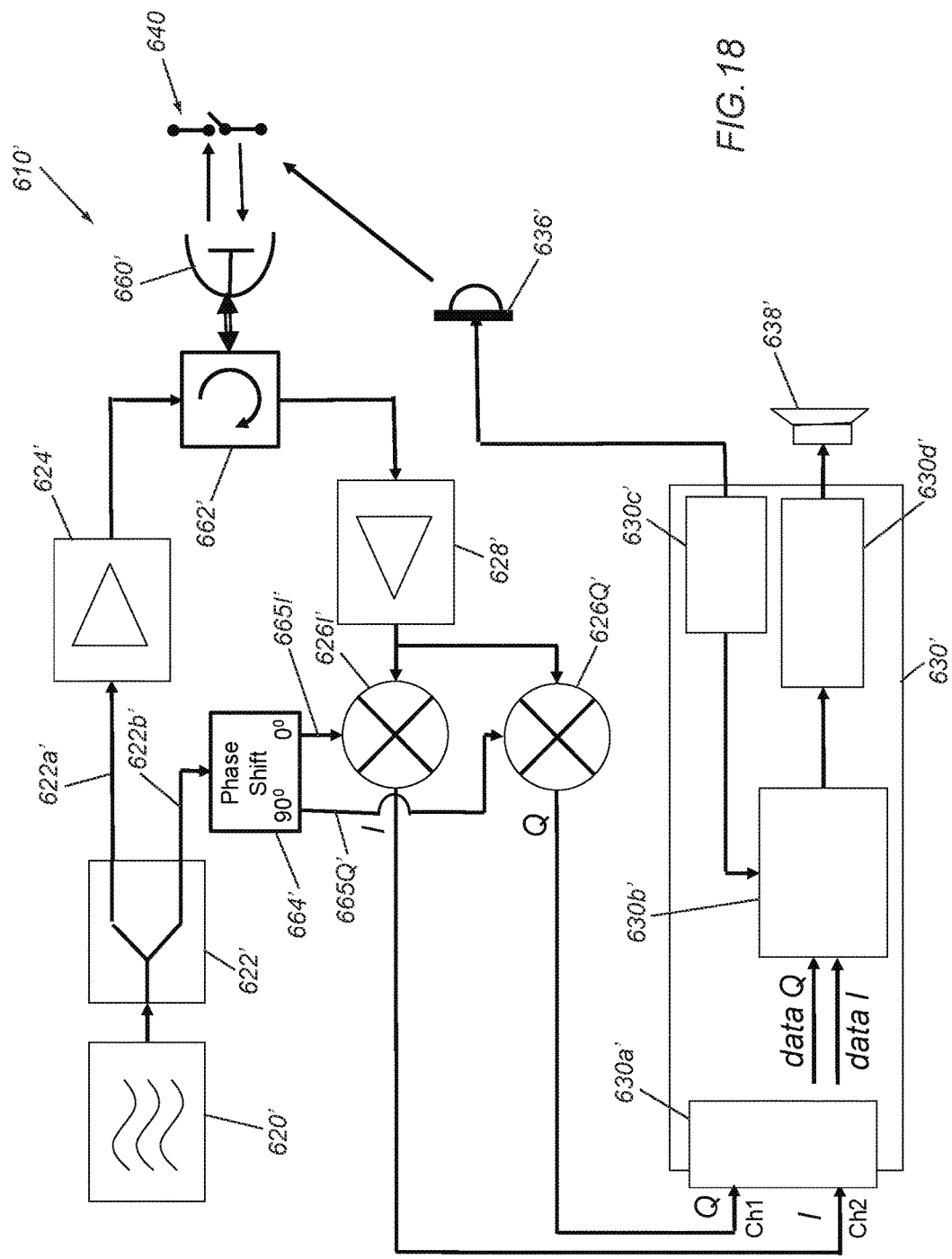
FIG. 18 is a schematic representation of components of an alternative embodiment of a system for identifying and providing range detection of a marker implanted within a patient's body.

The mixers 626I, 262Q use the input signals 665I, 665Q and return signal 674 to produce two intermediate frequency (IF) signals I and Q that contain components associated with the modulation of the amplitude and phase of the return signal 672, similar to the previous embodiments. The I and Q signals may then be band-pass filtered by filters 632I, 632Q and amplified by amplifiers 634U, 634Q, e.g., with the same gain IF amplifiers controlled by gain control 630e, and digitized simultaneously by ADC 630a for processing at the processor 630. Alternatively, as shown in FIG. 18, a system 610' may be provided in which a high resolution analog-to-digital converter 630a' is provided, which may avoid need for the band-pass filters 632 and amplifiers 634 (otherwise, system 610' includes similar components and functions similar to system 610). The processor 630 may include one or more microprocessors, controllers, and/or other components to control the various components and process the IF signals I, Q from the mixers 626I, 626Q.

Similar to other embodiments, the IR light from the LED(s) 636 causes the marker 640 to alternate between two form factors, e.g., opening and closing a switch (not shown)

coupled to antennas of the marker 640 to modulate the reflective properties of the marker 640. Due to the periodic switching of reflective properties of the marker 640 caused by periodic IR LED modulation, both quadrature components (I and Q) contain the modulation signal. The amplitudes of these modulation components in I and Q data are computed using an algorithm by the synchronous quadrature modulation detector 630 to get $I_A$ and $Q_A$, respectively. Then, the amplitude A associated with the RF signal attenuation and phase shift ($\varphi$) associated with the propagation delay may be computed as:

$$A = \sqrt{I_A^2 + Q_A^2} \quad \varphi = \operatorname{atan}\left(\frac{Q_A}{I_A}\right)$$

Using these quantities, the processor 630 may compute relative changes in propagation time and attenuation and, therefore, range change knowing propagation velocity or the range using a calibration method. The resulting values may be output to the user, e.g., via output controller 630d to one or more output devices 638 as an indicator of the location and/or distance from the probe to the marker 640.

Figure 19:
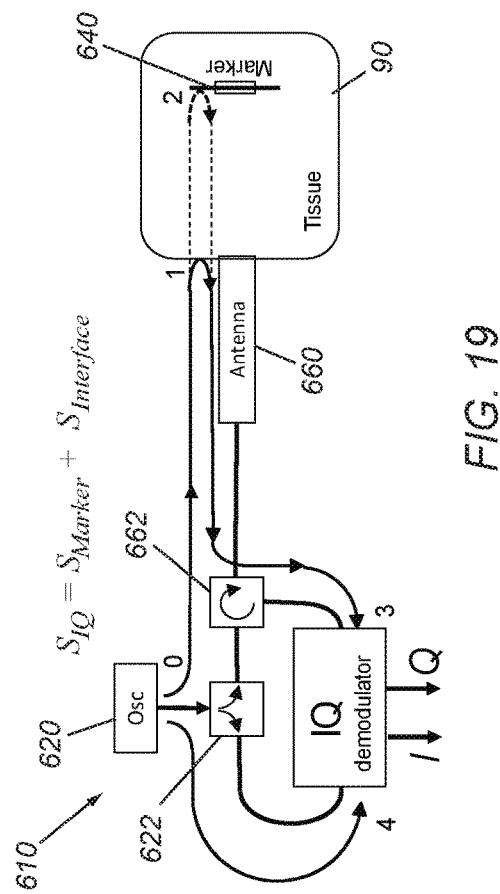
FIG. 19 is a schematic showing an exemplary method for range detection of a marker using the system of FIG. 17.

In an exemplary method, the system 610 may initially use amplitude of the return signal to identify and/or detect the marker 640, e.g., similar to other embodiments herein. Once the marker 640 has been identified, the system 610 may use both amplitude and phase shift to provide range detection, i.e., the distance from the antenna 660 to the marker 640. FIG. 19 is a schematic of the system 610 showing an exemplary method for range detection of the marker 640 implanted within tissue 90 using various paths defined by the system 610.

As shown in FIG. 19, IQ demodulator, which may include the phase splitter 664 and mixers 626I, 626Q shown in FIG. 17, produces quadrature components I and Q from the return signal from the marker 640 with respect to the transmit signal generated by the signal generator 620. The return signal ($S_{IQ}$) includes two components, $$S_{IQ} = S_{interface} + S_{marker},$$

where $S_{interface}$ is the signal resulting mostly from the propagation delay along path 0-1-3 in FIG. 19, i.e., from the signal generator 620 to the antenna 660 and back through the circulator 662 to the IQ demodulator, and $S_{marker}$ is the signal resulting from the propagation delay along path 0-2-3, i.e., from the signal generator 620 through the antenna 660 and tissue 90 to the marker 640 and back to the IQ demodulator, which are defined as:

$$S_{interface} = A_I \exp(i\, \lambda_C D_{013})$$

$$S_{marker} = A_M \exp(i\, \lambda_C D_{013} + i\, \lambda_T D_{121}),$$

where $D_{121}$ is twice the distance or range from the interface of the antenna 660 to the marker 640. $A_I$ and $A_M$ are complex amplitudes of the interface and marker reflections, respectively, capturing propagation attention and reflection phase shift, respectively. Due to relatively small reflection from the marker 640, $A_I \gg A_M$ and the phase of $S_{IQ}$ is mainly determined by the phase of $S_{interface}$. The value of $A_M$ amplitude changes in time due to modulation of the marker reflection by the light pulses, as described previously, and so may alternate between the following:

$$S_{IQ}^{IR\ on} = A_I \exp(i\, \lambda_C D_{013}) + A_M^{IR\ on} \exp(i\, \lambda_C D_{013} + i\, \lambda_T D_{121})$$

$$S_{IQ}^{IR\ off} = A_I \exp(i\, \lambda_C D_{013}) + A_M^{IR\ off} \exp(i\, \lambda_C D_{013} + i\, \lambda_T D_{121})$$

Figure 20A:
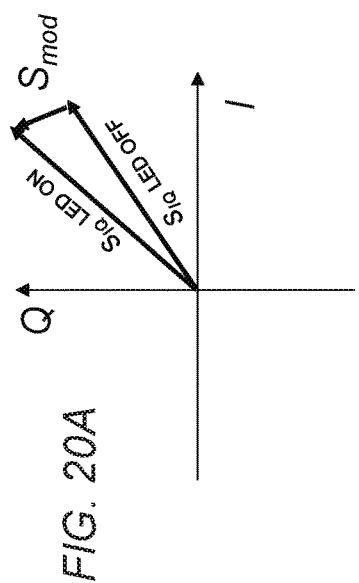
FIGS. 20A and 20B show exemplary I-Q output vectors that may be used in the method shown in FIG. 19.
Figure 20B:
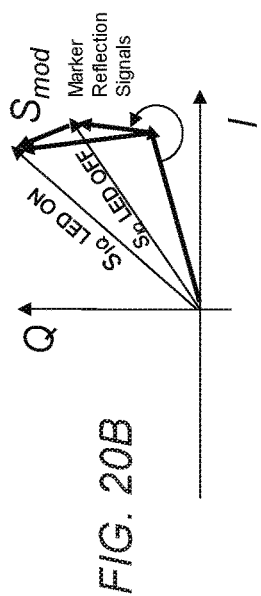

The IQ demodulator may take the original signal from the signal generator 620 (e.g., split by divider 622, shown in FIG. 17), corresponding to path 0-4 in FIG. 19, and mix it with signal 3 to produce two DC signals I and Q that can be considered as a vector in plane I, Q, e.g., as shown in FIGS. 20A and 20B. This vector changes as the reflection properties of the marker 640 changes due to the periodic light pulses turning on and off, e.g., between $S_{IQ\ LED\ on}$ and $S_{IQ\ LED\ off}$. Vector $S_{IQ}$ consists of two main components representing two reflections in the transmit-return path, i.e., $S_{interface}$ and $S_{marker}$, as described above. $S_{interface}$ includes environmental reflections, which is mostly a contribution from the antenna interface with the tissue surface and remains constant, while $S_{marker}$ represents the signal reflected from the marker 640.

The IQ demodulator may take the resulting vector components and use a best-fit approximation or other algorithm to provide an output corresponding to the range, i.e., distance from the antenna to the marker 640.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for localization of a marker within a target tissue region within a patient's body, comprising:
   a probe comprising one or more antennas for transmitting a radar signal into a patient's body towards a marker and receiving a reflected signal from the marker, and a light source for delivering infrared light pulses into the patient's body to cause the marker to change its reflective properties;
   a signal generator for generating a substantially continuous wave;
   a divider coupled to the signal generator for dividing the wave into first and second signals, the first signal delivered to the one or more antennas to transmit a substantially continuous transmit signal;
   a mixer coupled to the divider for receiving the second signal and coupled to the one or more antennas for receiving the reflected signal, the mixer mixing the second signal and the reflected signal to produce an IF (intermediate frequency) signal comprising components associated with modulation of amplitude and phase of the reflected signal caused by the infrared light pulses changing reflective properties of the marker; and
   a processor coupled to the mixer comprising a synchronous modulation detector that processes the IF signal to provide an output indicative of range from the one or more antennas to the marker based at least in part on the modulation of amplitude and phase synchronous with the infrared light pulses delivered by the light source.

2. The system of claim 1, further comprising an output device coupled to the processor for providing an output to a user corresponding to the range.

3. The system of claim 1, further comprising a first amplifier for amplifying the first signal from the power divider to generate the transmit signal transmitted by the one or more antennas.

4. The system of claim 3, further comprising a second amplifier coupled between the one or more antennas and the mixer for amplifying the reflected signal being delivered to the mixer.

5. The system of claim 1, wherein the one or more antennas comprise a transmit antenna coupled to the power divider for receiving the first signal and transmitting the transmit signal, and a receive antenna coupled to the mixer for receiving the reflected signal.

6. The system of claim 1, wherein the one or more antennas comprise a transmit/receive antenna and a circulator circuit coupled to the signal generator for delivering the first signal to the transmit/receive antenna and coupled to the mixer for delivering the return signal from the transmit/receive antenna to the mixer.

7. The system of claim 1, further comprising one or more filters and amplifiers coupled to the mixer and the processor for filtering and amplifying the IF signal delivered to the processor from the mixer.

8. The system of claim 7, further comprising an analog-to-digital converter for digitizing the IF signal from the mixer before processing by the synchronous modulation detector.

9. The system of claim 1, wherein the mixer is configured to remove high frequency components from the return signal corresponding to the wave to produce the IF signal.

10. The system of claim 1, wherein the marker comprises an energy converter configured to transform the infrared light pulses from the light source into electrical energy, and a switch coupled to the energy converter such that the energy pulses cause the switch to open and close to modulate the electromagnetic signals from the probe reflected by the marker.

11. A system for localization of a marker within a target tissue region within a patient's body, comprising:
a probe comprising one or more antennas for transmitting a radar signal into a patient's body towards a marker and receiving a reflected signal from the marker, and a light source for delivering infrared light pulses into the patient's body to cause the marker to change its reflective properties;
a signal generator for generating a substantially continuous wave;
a divider coupled to the signal generator for dividing the wave into first and second signals, the first signal delivered to the one or more antennas to transmit a substantially continuous transmit signal;
a phase splitter coupled to the divider for receiving the second signal creating a replica signal out of phase with the second signal;
first and second mixers coupled to the phase splitter for receiving the second signal and the replica signal, respectively, and coupled to the one or more antennas for receiving the reflected signal such that the first mixer mixes the second signal and the reflected signal and the second mixer mixes the replica signal and reflected signal to produce IF (intermediate frequency) signals comprising components associated with modulation of amplitude and phase of the reflected signal caused by the infrared light pulses changing reflective properties of the marker; and
a processor coupled to the mixers comprising a synchronous modulation detector that processes the IF signals to provide an output indicative of range from the one or more antennas to the marker based at least in part on the modulation of amplitude and phase synchronous with the infrared light pulses delivered by the light source.

12. The system of claim 11, wherein the first and second mixers are configured to remove high frequency components from the return signal corresponding to the wave to produce the IF signals.

13. The system of claim 11, further comprising one or more filters and amplifiers coupled to the mixers and the processor for filtering and amplifying the IF signals delivered to the processor from the mixers.

14. The system of claim 13, further comprising an analog-to-digital converter for simultaneously digitizing the IF signals from the mixers before processing by the synchronous modulation detector.

15. The system of claim 11, further comprising an output device coupled to the processor for providing an output to a user corresponding to the range.

16. The system of claim 11, further comprising a first amplifier for amplifying the first signal from the power divider to generate the transmit signal transmitted by the one or more antennas.

17. The system of claim 16, further comprising a second amplifier coupled between the one or more antennas and the mixer for amplifying the reflected signal being delivered to the mixer.

18. The system of claim 11, wherein the one or more antennas comprise a transmit antenna coupled to the power divider for receiving the first signal and transmitting the transmit signal, and a receive antenna coupled to the mixers for receiving the reflected signal.

19. The system of claim 11, wherein the one or more antennas comprise a transmit/receive antenna and a circulator circuit coupled to the signal generator for delivering the first signal to the transmit/receive antenna and coupled to the mixers for delivering the return signal from the transmit/receive antenna to the mixers.

20. The system of claim 11, wherein the processor is configured to process the IF signals to a) initially, identify the marker based on the modulation of amplitude in the return signal; and b) after identifying the marker, estimate a distance from the probe to the marker based on the modulation of amplitude and phase in the return signal.

21. The system of claim 11, wherein the marker comprises an energy converter configured to transform the infrared light pulses from the light source into electrical energy, and a switch coupled to the energy converter such that the energy pulses cause the switch to open and close to modulate the electromagnetic signals from the probe reflected by the marker.

* * * * *